(12) United States Patent
Thapliyal et al.

(10) Patent No.: US 6,379,351 B1
(45) Date of Patent: Apr. 30, 2002

(54) ELECTROSURGICAL METHOD FOR THE REMOVAL OF PACEMAKER LEADS

(75) Inventors: Hira V. Thapliyal, Los Altos, CA (US); Philip E. Eggers, Dublin, OH (US); Katherine M. Williams, Gilroy, CA (US); Michael A. Baker, Woodside, CA (US); Phillip M. Olsen, Sunnyvale, CA (US)

(73) Assignee: Arthrocare Corporation, Sunnyvale, CA (US)

( * ) Notice: Subject to any disclaimer, the term of this patent is extended or adjusted under 35 U.S.C. 154(b) by 0 days.

(21) Appl. No.: 09/507,366

(22) Filed: Feb. 18, 2000

Related U.S. Application Data

(63) Continuation of application No. 09/002,315, filed on Jan. 2, 1998, now Pat. No. 6,183,469.
(60) Provisional application No. 60/057,691, filed on Aug. 27, 1997.

(51) Int. Cl.[7] ............................................. A61B 18/14
(52) U.S. Cl. ...................... 606/41; 606/45; 606/48; 606/108; 607/122; 607/126; 604/35
(58) Field of Search ............................. 606/41, 45, 48, 606/108; 607/122, 126; 604/35

(56) References Cited

U.S. PATENT DOCUMENTS

| 4,033,351 A | 7/1977 | Hetzel ........................ 128/303 |
| 4,040,426 A | 8/1977 | Morrison, Jr. ............... 128/303 |
| 4,043,342 A | 8/1977 | Morrison Jr. ................ 128/303 |
| 4,116,198 A | 9/1978 | Roos .......................... 128/303 |

(List continued on next page.)

FOREIGN PATENT DOCUMENTS

| EP | 0368568 | 5/1990 | ............ A61N/1/05 |
| EP | 0703461 | 3/1996 | ............ G01R/27/02 |
| EP | 0740926 | 11/1996 | ............ A61B/17/39 |

(List continued on next page.)

OTHER PUBLICATIONS

L. Satler (1996) *Catheterization and Cardiovascular Diagnosis* 37:320–321.
O. Topaz et al. (1996) *Catheterization and Cardiovascular Diagnosis* 37:293–299.

(List continued on next page.)

*Primary Examiner*—Lee Cohen
(74) *Attorney, Agent, or Firm*—John T. Raffle

(57) ABSTRACT

The present invention is directed to systems, methods and apparatus for removing implanted objects from a patient's body, particularly implanted endocardial or epicardial pacemaker leads and transvenous defibrillation leads from a patient's heart. In one aspect of the invention, an electrosurgical catheter is advanced to a position within the thoracic cavity adjacent a portion of a pacemaker lead that is affixed to heart tissue. Preferably, the catheter is advanced over the pacemaker lead, i.e., using the pacemaker lead as a guidewire, to facilitate this positioning step. Once the distal end of the catheter reaches a blockage, or a portion of the lead that is attached to fibrous scar tissue, a high frequency voltage difference is applied between one or more electrode terminal(s) at the distal end of the catheter and one or more return electrode(s) to remove the scar tissue around the lead. The catheter is then advanced further along the lead until it reaches another blockage caused by fibrous scar tissue, and the process is continued until the catheter reaches the distal tip of the lead in the myocardium. At this point, the distal tip may be severed from the rest of the lead, or pulled out of the myocardial tissue in a conventional manner. The scar tissue around the pacemaker lead is precisely ablated before removing the lead, which minimizes or eliminates the risks associated with mechanical traction and countertraction, such as disruption of the heart wall, lead breakage with subsequent migration and the like.

17 Claims, 22 Drawing Sheets

U.S. PATENT DOCUMENTS

| | | | |
|---|---|---|---|
| 4,202,337 A | 5/1980 | Hren et al. | 128/303 |
| 4,228,800 A | 10/1980 | Degler Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,476,862 A | 10/1984 | pao | 128/303 |
| 4,532,924 A | 8/1985 | Auth et al. | 128/303 |
| 4,548,207 A | 10/1985 | Reimels | 128/303 |
| 4,582,056 A | 4/1986 | McCorkle, Jr. | 128/303 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,765,331 A | 8/1988 | Petruzzi et al. | 128/303 |
| 4,823,791 A | 4/1989 | D'Amelio | 123/303 |
| 4,976,711 A | 12/1990 | Parins et al. | 606/48 |
| 4,998,933 A | 3/1991 | Eggers et al. | 606/41 |
| 5,007,908 A | 4/1991 | Rydell | 606/47 |
| 5,009,656 A | 4/1991 | Reimels | 128/303 |
| 5,078,717 A | 1/1992 | Parins et al. | 606/48 |
| 5,078,736 A | 1/1992 | Behl | 623/1 |
| 5,083,565 A | 1/1992 | Parins | 128/642 |
| 5,098,431 A | 3/1992 | Rydell | 606/48 |
| 5,108,391 A | 4/1992 | Flacheneker et al. | 606/38 |
| 5,122,138 A | 6/1992 | Manwaring | 606/46 |
| 5,125,928 A | 6/1992 | Parins et al. | 606/48 |
| 5,178,620 A | 1/1993 | Eggers et al. | 606/41 |
| 5,190,517 A | 3/1993 | Zieve et al. | 604/22 |
| 5,190,540 A | 3/1993 | Lee | 606/28 |
| 5,195,959 A | 3/1993 | Smith | 604/34 |
| 5,197,963 A | 3/1993 | Parins | 606/46 |
| 5,217,457 A | 6/1993 | Delahuerga et al. | 606/42 |
| 5,222,938 A | 6/1993 | Behl | 604/49 |
| 5,246,438 A | 9/1993 | Langberg | 606/33 |
| 5,267,994 A | 12/1993 | Gentelia et al. | 606/15 |
| 5,267,997 A | 12/1993 | Farin et al. | 606/38 |
| 5,281,216 A | 1/1994 | Klicek | 606/42 |
| 5,281,218 A | 1/1994 | Imran | 606/41 |
| 5,300,069 A | 4/1994 | Hunsberger et al. | 606/37 |
| 5,312,400 A | 5/1994 | Bales et al. | 606/41 |
| 5,314,406 A | 5/1994 | Arias et al. | 604/21 |
| 5,330,470 A | 7/1994 | Hagen | 606/42 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,380,277 A | 1/1995 | Phillips | 604/33 |
| 5,383,917 A | 1/1995 | Desai et al. | 607/702 |
| 5,395,312 A | 3/1995 | Desai | 604/22 |
| 5,417,687 A | 5/1995 | Nardella et al. | 606/32 |
| 5,419,767 A | 5/1995 | Eggers et al. | 604/114 |
| 5,423,806 A | 6/1995 | Dale et al. | 606/15 |
| 5,429,604 A | 7/1995 | Hammersmark et al. | 604/95 |
| 5,454,809 A | 10/1995 | Janssen | 606/41 |
| 5,456,680 A | 10/1995 | Taylor et al. | 606/6 |
| 5,484,433 A | 1/1996 | Taylor et al. | 606/17 |
| 5,514,128 A | 5/1996 | Hillsman et al. | 606/7 |
| 5,514,130 A | 5/1996 | Baker | 606/41 |
| 5,542,928 A | 8/1996 | Evans et al. | 604/113 |
| 5,545,161 A | 8/1996 | Imran | 606/41 |
| 5,556,397 A | 9/1996 | Long et al. | 606/48 |
| 5,569,242 A | 10/1996 | Lax et al. | 606/42 |
| 5,584,872 A | 12/1996 | LaFontaine et al. | 607/116 |
| 5,609,151 A | 3/1997 | Mulier et al. | 128/642 |
| 5,626,576 A * | 5/1997 | Janssen | 606/41 |
| 5,643,251 A | 7/1997 | Hillsman et al. | 606/7 |
| 5,647,869 A | 7/1997 | Goble et al. | 606/37 |
| 5,673,695 A | 10/1997 | McGee et al. | 128/642 |
| 5,676,693 A | 10/1997 | LaFontaine | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,725,524 A | 3/1998 | Mulier et al. | 606/41 |
| 5,766,153 A | 6/1998 | Eggers et al. | 604/114 |
| 5,779,715 A | 7/1998 | Tu | 606/108 |
| 5,807,395 A | 9/1998 | Mulier et al. | 606/41 |
| 5,810,764 A | 9/1998 | Eggers et al. | 604/23 |
| 5,817,013 A | 10/1998 | Ginn et al. | 600/114 |
| 5,823,955 A | 10/1998 | Kuck et al. | 600/374 |
| 5,836,946 A * | 11/1998 | Diaz et al. | 606/45 |
| 5,840,059 A | 11/1998 | March et al. | 604/53 |
| 5,860,951 A | 1/1999 | Eggers et al. | 604/49 |
| 5,860,974 A | 1/1999 | Abele | 606/41 |
| 5,873,855 A | 2/1999 | Eggers et al. | 604/114 |
| 5,885,277 A | 3/1999 | Korth | 606/35 |
| 5,897,553 A | 4/1999 | Mulier et al. | 606/41 |
| 5,910,150 A | 6/1999 | Saadat | 606/159 |
| 5,944,715 A | 8/1999 | Goble et al. | 606/41 |
| 5,980,515 A * | 11/1999 | Tu | 606/41 |

FOREIGN PATENT DOCUMENTS

| | | | |
|---|---|---|---|
| EP | 0754437 | 1/1997 | A61B/17/39 |
| EP | 0812575 | 12/1997 | A61B/17/39 |
| GB | 2308979 | 7/1997 | A61B/17/39 |
| GB | 2308980 | 7/1997 | A61B/17/36 |
| GB | 2308981 | 7/1997 | A61B/17/39 |
| GB | 2327350 | 1/1999 | A61B/17/39 |
| GB | 2327351 | 1/1999 | A61B/17/39 |
| GB | 2327352 | 1/1999 | A61B/17/39 |
| JP | 57-117843 | 7/1982 | A61B/17/39 |
| WO | 90/07303 | 7/1990 | A61B/17/39 |
| WO | 93/20747 | 10/1993 | A61B/5/00 |
| WO | 94/26228 | 11/1994 | A61G/17/36 |
| WO | 95/33513 | 12/1995 | A61N/1/05 |
| WO | 95/34259 | 12/1995 | A61F/5/48 |
| WO | 96/35469 | 11/1996 | A61M/25/00 |
| WO | 97/00646 | 1/1997 | A61B/17/39 |
| WO | 97/00647 | 1/1997 | A61B/17/39 |
| WO | 97/24073 | 7/1997 | A61B/17/39 |
| WO | 97/24993 | 7/1997 | A61B/17/39 |
| WO | 97/24994 | 7/1997 | A61B/17/39 |
| WO | 97/48346 | 12/1997 | A61B/17/39 |
| WO | 98/23324 | 6/1998 | A61N/1/05 |

OTHER PUBLICATIONS

C. Slager et al. (1987) *Z. Kardiologie* 76 (6) :67–71.

C. Slager et al. (1985) *JACC* 5(6) :1382–6.

E. Kramolowsky et al. (1991) *J. of Urology* 146:669–674.

R. Tucker et al. (1990) *Urol. Res.* 18:291–294.

R. Tucker et al. (1989) *J. of Urology* 141:662–665.

R. Tucker et al. (1989) Abstract P14–11, 7th World Congress on Endourology and ESWL, Nov. 27–30, 1989, Kyoto, Japan.

P. Nardella (1989) *SPIE* 1068:42–49.

Elsasser et al. (1976) *Medizinal–Markt/Acta Medicotechnica* 24 (4) :129–134.

J. Rand et al. (1985) *J. of Arthroscopy* 1(4) :242–246.

* cited by examiner

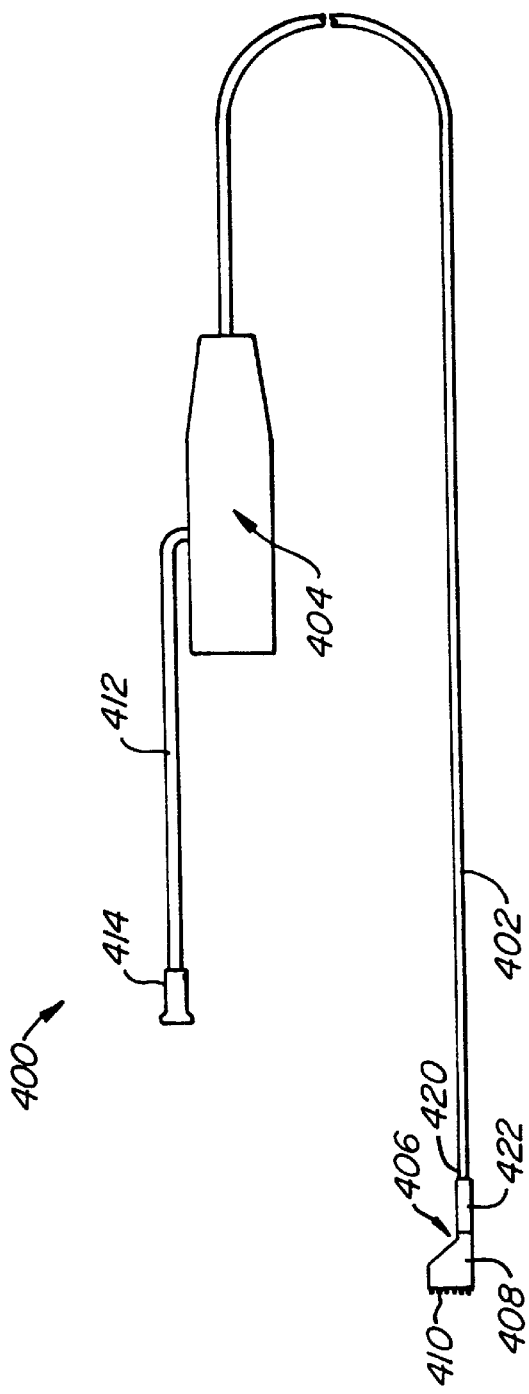
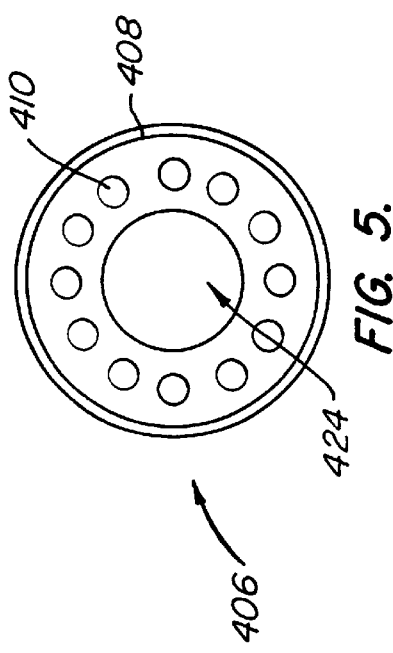
FIG. 4.
FIG. 5.

ELECTROSURGICAL METHOD FOR THE REMOVAL OF PACEMAKER LEADS

CROSS-REFERENCE TO RELATED APPLICATIONS

The present application is a continuation of Ser. No. 09/002,315 filed Jan. 2, 1998 now U.S. Pat. No. 6,183,469 which is a continuation-in-part of Provisional Application No. 60/057,691 filed Aug. 27, 1997, the complete disclosure of which is incorporated herein by reference.

The present invention is related to commonly assigned Provisional Application Nos. 60/062,997 and 60/062,996 both filed on Oct. 23, 1997, application Ser. No. 08/942,580 filed Oct. 2, 1997, now U.S. Pat. No. 6,159,194. U.S. application Ser. No. 08/753,227, filed on Nov. 22, 1996, U.S. application Ser. No. 08/687,792, filed on Jul. 18, 1996, and U.S. Pat. No. 5,697,909, filed on May 10, 1994, which was a continuation-in-part of application Ser. No. 08/059,681, filed on May 10, 1993, which was a continuation-in-part of application Ser. No. 07/958,977, filed on Oct. 9, 1992 which was a continuation-in-part of application Ser. No. 07/817,575, filed on Jan. 7, 1992, the complete disclosures of which are incorporated herein by reference for all purposes. The present invention is also related to commonly assigned U.S. Pat. Nos. 5,683,366, and 5,697,281 the complete disclosures of which are incorporated herein by reference for all purposes.

BACKGROUND OF THE INVENTION

The present invention is directed to electrosurgical systems, apparatus and methods for removing an implanted object from a patient's body, and specifically to systems and methods for the removal of implanted endocardial or epicardial pacemaker leads or transvenous defibrillation leads from a patient's heart and the venous paths thereto.

Various types of pacemaker leads and their electrodes are introduced into different chambers of the heart, including the right ventricle, right atrial appendage, the atrium and the coronary sinus, although the majority of pacemaker leads are implanted in the right ventricle or appendage thereof. These flexible leads provide an electrical. pathway between a pulse generator, connected to the proximal end of the lead, and the heart tissue, which is in contact with the distal end or electrode of the lead. Electrical pulses emitted by the pacemaker travel through the pacemaker lead and stimulate the heart to restore healthy heart rhythms for patient's whose hearts are beating irregularly.

Pacemaker leads usually comprise an insulating sleeve that contains a coiled conductor having an electrode tip at the distal end. This electrode tip is often placed in contact with the endocardial or myocardial tissue by passage through a venous access, such as the subclavian vein or one of its tributaries, which leads to the endocardial surface of the heart chambers. The electrode tip is held in place within the trabeculations of myocardial tissue. The distal ends of many available leads include flexible tines, wedges or finger-like projections which project radially outward to help prevent dislodgment of the lead tip from the cardial tissue.

Once an endocardial lead is implanted within a heart chamber, the body's reaction to its presence furthers its fixation within the heart. Shortly after placement, blood clots form about the flanges or tines due to enzymes released in response to the irritation of the cardial tissue caused by the electrode tip. Over time, fibrous scar tissue eventually forms over the distal end, usually in three to six months. In addition, fibrous scar tissue often forms, at least in part, over the insulator sleeve within the venous system and the heart chamber.

Endocardial leads occasionally malfunction, due to a variety of reasons, including lead block, insulation breaks, breakage of the inner helical coil conductor, etc. In addition, it is sometimes desirable to electronically stimulate different portions of the heart than that being stimulated with leads already in place. Due to these and other factors, a considerable number of patients may eventually have more than one, and sometimes as many as four or five, unused leads in their venous systems and heart. These unused leads often develop complications, such as infection, septicemia, or endocarditis. In addition, unused leads may entangle over time, thereby increasing the likelihood of blood clot formation, which may embolize to the lung and produce severe complications or even fatality. Further, the presence of unused leads in the venous pathway and inside the heart may cause considerable difficulty in the positioning and attachment of new endocardial leads in the heart.

Conventional techniques for removing unused pacemaker leads are also associated with serious risks. Standard mechanical traction and, more often, intravascular mechanical countertraction are the methods most commonly used at present (notably the system manufactured by Cook Pacemaker Corporation). External mechanical traction involves grasping the proximal end of the lead and pulling. This process is repeated daily, usually a few millimeters of the lead are removed from the patient each day, with progress monitored by chest radiography. Internal mechanical traction is accomplished by exerting traction (manual or sustained) on the lead via a snare, forceps or other retrieval catheter that has grasped the lead within the venous system. These techniques, however, can cause disruption of the heart wall prior to release of the affixed lead tip, causing fatality, or other complications, such as lead breakage with subsequent migration, myocardial avulsion or avulsion of a tricuspid valve leaflet. Moreover, lead removal may further be prevented by a channel of fibrotic scar tissue and endothelium surrounding the outer surface of the lead body or insulator sleeve at least part way along the venous pathway. Such channel scar tissue inhibits withdrawal of the lead because it is encased within the scar tissue. Continual pulling or twisting of the proximal free end of the lead could cause rupturing of the right atrial wall or right ventricular wall.

Intravascular countertraction is accomplished by applying traction on the lead while countering this traction by the circumference of dilator sheaths advanced over the lead. While maintaining sufficient traction on the lead to guide the sheaths, a pair of sheaths is advanced over the lead toward the myocardium to dislodge scar tissue from the lead. If insufficient tension is placed on the lead, however, the method is no longer countertraction but reduced to external traction with the aforementioned risks. In addition, misdirected countertraction along the lead body may tear the vein or heart wall.

In an effort to overcome some of the problems associated with mechanical traction and intravascular countertraction lead removal methods, lasers have been developed for extracting pacemaker leads. In some of these techniques, catheters having laser fibers at their distal end are advanced over the pacemaker lead to the site of attachment. The laser fibers are then energized to separate the lead from the fibrous scar tissue. These devices are described in U.S. Pat. Nos. 5,423,806, 5,643,251, 5,514,128 and 5,484,433. The standard laser light source for these devices is the xenonchloride excimer laser, which is commercially available from Spectranetics Corporation of Colorado Springs, Colo.

Conventional electrosurgery methods have not been successful in removing pacemaker leads. One of the factors which appears to create the greatest impediment to electrosurgical removal of pacemaker leads is scar tissue. Scar tissue exhibits much lower thermal conductivity and electrical conductivity than normal (e.g., myocardial) tissue. Since conventional electrosurgery generally relies on the conduction of electrical currents through the target tissue being cut or vaporized, conventional electrosurgery has failed to remove this scar tissue. In fact, previous attempts to use conventional electrosurgery methods to remove pacemaker leads have resulted in current flow and thermal effects in the "healthy" tissue surrounding the scar tissue mass, but not in the scar tissue mass itself. As a result, the targeted scar tissue was not affected and the lead was not removable.

SUMMARY OF THE INVENTION

The present invention is directed to systems, methods and apparatus for removing implanted objects from a patient's body, particularly implanted objects attached to fibrous scar tissue. The systems and methods of the present invention are particularly useful for removing implanted endocardial or epicardial pacemaker leads or transvenous defibrillation leads from a patient's heart.

Methods of the present invention comprise positioning one or more electrode terminal(s) adjacent an implanted object attached to tissue and applying a sufficient high frequency voltage difference between the electrode terminal(s) and one or more return electrode(s) to detach the implanted object from the tissue. The high frequency voltage is typically sufficient to ablate or remove a portion of the tissue between the implanted object and the remaining tissue so that the implanted object can then be removed without pulling or tearing the patient's tissue. In preferred embodiments, an electrically conductive fluid, such as isotonic saline or conductive gas, is delivered to the target site around the pacemaker lead to substantially surround the electrode terminal(s) with the fluid. Alternatively, a more viscous fluid, such as an electrically conductive gel, may be delivered or applied directly to the target site such that the electrode terminal(s) are immersed within the gel during the procedure. In both embodiments, high frequency voltage is applied between the electrode terminal(s) and one or more return electrode(s) to remove at least a portion of the tissue.

In one aspect of the invention, an electrosurgical catheter is advanced to a position within the thoracic cavity adjacent a portion of a pacemaker lead that is affixed to heart tissue. Preferably, the catheter is advanced over the pacemaker lead, i.e., using the pacemaker lead as a guidewire, to facilitate this positioning step. Once the distal end of the catheter reaches a blockage, or a portion of the lead that is attached to fibrous scar tissue, a high frequency voltage difference is applied between one or more electrode terminal(s) at the distal end of the catheter and one or more return electrode(s) to remove the scar tissue around the lead. Depending on the configuration of the distal end of the catheter, the electrode terminal(s) may be rotated, oscillated or otherwise manipulated to facilitate the removal of tissue between the lead and the heart. The catheter is then advanced further along the lead until it reaches another blockage caused by fibrous scar tissue, and the process is continued until the catheter reaches the distal tip of the lead in the myocardium. At this point, the distal tip may be severed from the rest of the lead, or pulled out of the myocardial tissue in a conventional manner. Alternatively, the catheter may be energized and advanced through the myocardial tissue to form an annular channel around a portion of the distal tip. If the distal tip includes flanges or tines, these tines may be severed with the electrical energy, and the remainder of the distal tip removed from the myocardial tissue.

In a specific configuration, the fibrous scar tissue is removed by molecular dissociation or disintegration processes. In these embodiments, the high frequency voltage applied to the electrode terminal(s) is sufficient to vaporize an electrically conductive fluid (e.g. gel or saline) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366, the complete disclosure of which is incorporated herein by reference.

The present invention offers a number of significant advantages over current techniques for removing pacemaker leads. For one thing, the scar tissue around the pacemaker lead is precisely ablated before removing the lead, which minimizes or eliminates the risks associated with mechanical traction and countertraction, such as disruption of the heart wall, lead breakage with subsequent migration and the like. In addition, the ability to precisely control the volumetric removal of tissue results in tissue ablation or removal that is very defined, consistent and predictable. The shallow depth of tissue heating also helps to minimize or completely eliminate thermal damage to the heart. In particular, since the mechanism for removing or ablating the scar tissue does not rely primarily on electrical current flow through the scar tissue, the low electrical conductivity of the scar tissue (relative to the adjacent heart tissue) does not effect the removal of this tissue. In addition, since the electrical current primarily flows back to the return electrode through the electrically conductive fluid, current flow into healthy heart tissue is minimized. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as other fluids.

Apparatus of the present invention comprise a catheter shaft having a flexible body with a proximal end portion and a distal end portion having a distal opening. The catheter shaft has an inner lumen coupled to the distal opening and sized to accommodate a pacemaker lead, usually about 0.2 to 10 mm diameter and preferably about 0.5 to 5 mm in diameter. The catheter body has one or more electrode terminal(s) on the shaft at the distal end portion, and a connector extending through the body for coupling the electrode terminal(s) to a source of high frequency electrical energy.

The apparatus will preferably further include one or more fluid delivery element(s) for delivering electrically conducting fluid to the electrode terminal(s) and the target site. The fluid delivery element(s) may be located on the catheter, e.g., one or more fluid lumen(s) or tube(s), or they may be part of a separate instrument. Alternatively, an electrically conducting gel or spray, such as a saline electrolyte or other conductive gel, may be applied the target site. In this embodiment, the apparatus may not have a fluid delivery element. In both embodiments, the electrically conducting fluid will preferably generate a current flow path between the electrode terminal(s) and one or more return electrode(s). In an exemplary embodiment, the return electrode(s) are located on the catheter and spaced a sufficient distance from the electrode terminal(s) to substantially avoid or minimize current shorting therebetween and to shield the return electrode(s) from tissue at the target site. Alternatively, the return electrode(s) may comprise a dispersive pad located on the outer surface of the patient (i.e., a monopolar modality).

In a specific configuration, the apparatus includes a plurality of electrically isolated electrode terminals extending from the distal end of the catheter shaft. The electrode terminals are each mounted within an electrically insulating support member, and spaced peripherally around the distal opening of the catheter body. In these embodiments, the catheter may include a single, annular return electrode located proximal of the distal opening, or a plurality of electrode terminals mounted to the support members proximal of the electrode terminals. The latter embodiment has the advantage that the electric currents are confined to a distal region of the catheter body, which may facilitate advancement of the catheter through fibrous scar tissue. In this embodiment, the catheter body also includes one or more fluid delivery lumens spaced peripherally around the central lumen for delivering electrically conductive fluid to the electrode terminals. In addition, the catheter body will preferably include one or more suction lumens spaced peripherally around the central lumen, and suitably coupled to an external suction source for aspirating fluid, tissue and/or gaseous products of ablation (e.g., non-condensible gases) from the target site.

In one embodiment, the catheter includes a lateral port, opening or slit proximal to the distal end of the catheter (typically about 0.5 to 10 cm), and sized for receiving the pacemaker lead therethrough. In this embodiment, the pacemaker lead is loaded through the distal opening into the inner lumen of the catheter, and out through the lateral port so that the lead only extends through a distal end portion of the catheter body. This side port loading feature makes it easier to advance the catheter body over the pacemaker lead, and provides the physician with more control of the distal end portion. For example, this enhanced control allows the physician to rotate the distal end of the catheter relative to the pacemaker lead and the fibrous scar tissue to facilitate the removal of an annular channel of scar tissue around the lead (e.g., the electrode terminals are energized and rotated to ablate or remove an annular channel of tissue). In this embodiment, the connectors for the electrode terminal(s) and the return electrode(s) are preferably flat tape wires that extend around the periphery of the distal end portion, and around the lateral port to the proximal end of the catheter body.

BRIEF DESCRIPTION OF THE DRAWINGS

FIG. 4 illustrates one embodiment of an electrosurgical catheter for the removal of pacemaker leads according to the present invention;

FIG. 5 is a distal end view of the catheter of FIG. 4;

DESCRIPTION OF SPECIFIC EMBODIMENTS

Figure 1:
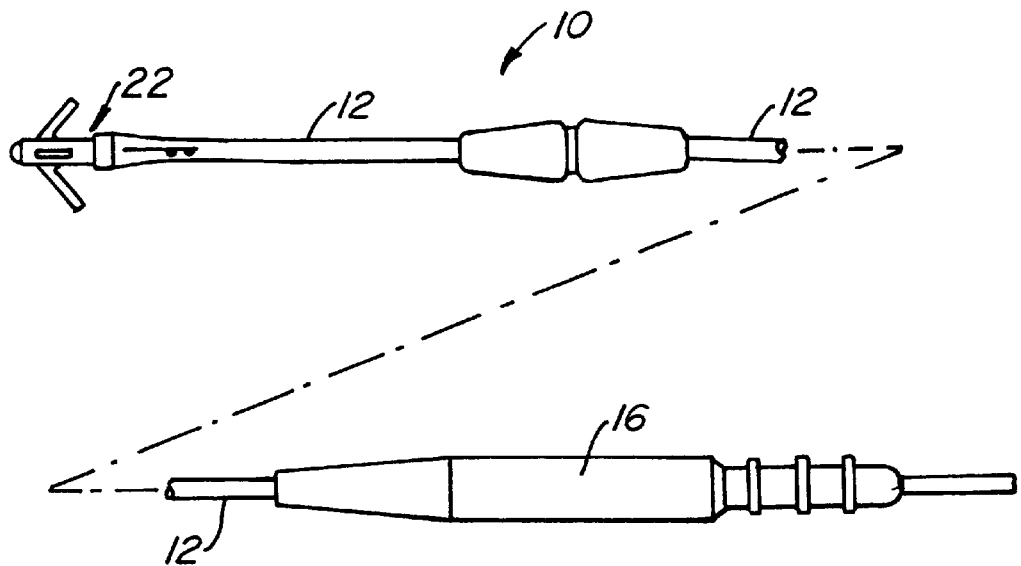
FIG. 1 illustrates a conventional pacemaker lead incorporating tines to anchor the tip of the pacemaker lead into the heart wall.

The present invention relates generally to the field of electrosurgery, and more particularly to surgical devices, systems and methods which employ high frequency electrical energy to remove or ablate tissue attached to implanted objects within the body. The systems and methods of the present invention are particularly useful for removing implanted endocardial or epicardial pacemaker leads or transvenous defibrillation leads from a patient's heart. In addition to pacemaker lead removal, the present invention may be used in body lumens, e.g., for removing atheromatous material which partially or fully occludes the body lumen, such as a blood vessel or for removing stents or other implanted objects. Moreover, other body lumens that may be treated by the method and apparatus of the present invention include the urinary tract (which for example may be occluded by an enlarged prostrate in males), the fallopian tubes (which may be occluded and cause infertility), and the like. In fact, the methods and apparatus disclosed herein may be used in a wide variety of procedures, including open procedures, intravascular procedures, urology, laparoscopy, arthroscopy, thoracoscopy or other cardiac procedures, dermatology, orthopedics, gynecology, otorhinolaryngology, spinal and neurologic procedures, oncology and the like. For convenience, the remaining disclosure will be directed specifically to the removal of pacemaker leads from the heart.

In the present invention, high frequency (RF) electrical energy is applied to one or more electrode terminals (usually in the presence of electrically conductive fluid) to remove and/or modify the structure of tissue structures. Depending on the specific procedure, the present invention may be used to: (1) volumetrically remove tissue (i.e., ablate or effect molecular dissociation of the tissue structure); (2) cut or resect tissue; (3) vaporize, cauterize or desiccate tissue and/or (4) coagulate and seal severed blood vessels.

In the preferred method of the present invention, tissue around an implanted object, such as fibrous scar tissue, is volumetrically removed or ablated. In this procedure, a high frequency voltage difference is applied between one or more electrode terminal(s) and one or more return electrode(s) to develop high electric field intensities in the vicinity of the target tissue. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid, such as isotonic saline or blood, delivered to the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena, termed Coblation™ can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

The present invention is also useful for removing or ablating tissue around nerves, such as spinal, visceral or cranial nerves, e.g., the olfactory nerve on either side of the nasal cavity, the optic nerve within the optic and cranial canals, the palatine nerve within the nasal cavity, soft palate, uvula and tonsil, etc. One of the significant drawbacks with prior art mechanical cutters and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers. A more complete description of this phenomena can be found in co-pending U.S. Patent Application entitled "Systems and Methods for Endoscopic Sinus Surgery", filed Dec. 15, 1997, the complete disclosure of which is incorporated herein by reference.

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The electrosurgical instrument will comprise a shaft having a proximal end and a distal end which supports one or more electrode terminal(s). The shaft may assume a wide variety of configurations, with the primary purpose being to mechanically support one or more electrode terminal(s) and permit the treating physician to manipulate the electrode(s) from a proximal end of the shaft. Usually, an electrosurgical probe shaft will be a narrow-diameter rod or tube, more usually having dimensions which permit it to be introduced into a body cavity, such as the thoracic cavity, through an associated trocar or cannula in a minimally invasive procedure, such as arthroscopic, laparoscopic, thoracoscopic, and other endoscopic procedures. Thus, the probe shaft will typically have a length of at least 5 cm for open procedures and at least 10 cm, more typically being 20 cm, or longer for endoscopic procedures. The probe shaft will typically have a diameter of at least 1 mm and frequently in the range from 1 to 10 mm.

The electrosurgical probe may be delivered percutaneously (endoluminally) to the ventricular cavity of the heart by insertion through a conventional or specialized guide catheter, or the invention may include a catheter having an active electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The shaft will usually include a plurality of wires or other conductive elements running axially therethrough to permit connection of the electrode or electrode array and the return electrode to a connector at the proximal end of the shaft. The catheter may include a guide wire for guiding the catheter to the target site, or the catheter may comprise a steerable guide catheter. In the preferred configuration, the pacemaker lead will be used as the guide wire, as discussed below. The catheter may also include a substantially rigid distal end portion to increase the torque control of the distal end portion as the catheter is advanced further into the patient's body. Specific shaft designs will be described in detail in connection with the figures hereinafter.

The electrode terminal(s) are preferably supported within or by an inorganic insulating support positioned near the distal end of the instrument shaft, e.g., a catheter body. The return electrode may be located on the catheter body, on another instrument, on the external surface of the patient (i.e., a dispersive pad), or the return electrode may be the lead tip itself. The likely presence of scar tissue surrounding the lead tip, however, will usually limit use of the lead as the return electrode due to inadequate current flow through the small exposed area of lead at the tip, and the potentially high electrical impedance of the surrounding scar tissue. In addition, the close proximity of the heart makes a bipolar design more preferable (i.e., no dispersive pad). Accordingly, the return electrode is preferably either integrated with the catheter body, or another instrument located in close proximity to the distal end of the catheter body. The proximal end of the catheter will include the appropriate electrical connections for coupling the return electrode(s) and the electrode terminal(s) to a high frequency power supply, such as an electrosurgical generator.

In the representative embodiment, the catheter will have an internal lumen sized to accommodate the pacemaker lead, so that the catheter can be advanced over the lead to the fibrous scar tissue. The diameter of the internal lumen will vary according to the pacemaker lead diameter, which typically range in diameter from about 0.2 to 10.0 mm, usually 0.5 to 5.0 mm, often about 1.1 to 3.3 mm. Of course, the catheter of the present invention may be modified to accommodate newly designed pacemaker leads (e.g., with larger or small diameters). The internal lumen may extend the entire length of the catheter, or only partway along the length of the catheter. In the latter embodiment, the catheter will include a side port or opening so that the pacemaker lead can be fed through the side port in a rapid exchange procedure to advance the catheter along the lead. In order to provide maximum torque control, it may be preferable to insert the distal end of the catheter over the entire length of pacemaker lead rather than limiting the "lead following lumen" within the distal end to a relatively short length (e.g., 10 cm) from the working end of the catheter.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above.

In some procedures, it may also be necessary to retrieve or aspirate the electrically conductive fluid and/or the non-condensible gaseous products of ablation. For example, in procedures in and around the heart, or within blood vessels, it may be desirable to aspirate the fluid so that it does not flow downstream. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include one or more suction lumen(s) in the probe, or on another instrument, coupled to a suitable vacuum source for aspirating fluids from the target site.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow into the heart or lungs. In addition, it may be desirable to limit the amount of suction to limit the undesirable effect suction may have on hemostasis of severed blood vessels within heart tissue.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels. The electrically conducting fluid should have a threshold conductivity to provide a suitable conductive path between the return electrode and the electrode terminal (s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). For removal of pacemaker leads attached to heart tissue, the voltage will usually be in the range of about 100 to 300 Vrms. Typically, the peak-to-peak voltage will be in the range of 10 to 2000 volts and preferably in the range of 20 to 500 volts and more preferably in the range of about 40 to 450 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular cardiac surgery, arthroscopic surgery, dermatological procedure, ophthalmic procedures, open surgery or other endoscopic surgery procedure. For cardiac procedures, the power source may have an additional filter, for filtering leakage voltages at frequencies below 100 kHz, particularly voltages around 60 kHz. A description of a suitable power source can be found in "SYSTEMS AND METHODS FOR ELECTROSURGICAL TISSUE AND FLUID COAGULAION", Ser. No. 60/062,997 filed on Oct. 23, 1997.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

In yet another aspect of the invention, the control system is "tuned" so that it will not apply excessive power to the blood (e.g., in the ventricle), once it crosses the wall of the heart and enters the chamber of the left ventricle. This minimizes the formation of a thrombus in the heart (i.e., will not induce thermal coagulation of the blood). The control system may include an active or passive architecture, and will typically include a mechanism for sensing resistance between a pair(s) of active electrodes at the distal tip, or between one or more active electrodes and a return electrode, to sense when the electrode array has entered into the blood-filled chamber of the left ventricle. Alternatively, current limiting means may be provided to prevent sufficient joulean heating in the lower resistivity blood to cause thermal coagulation of the blood. In another alternative embodiment, an ultrasound transducer at the tip of the probe can be used to detect the boundary between the wall of the heart and the blood filled left ventricle chamber, turning off the electrode array just as the probe crosses the boundary.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the catheter may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter or probe comprises a single active electrode terminal that extends from an insulating member, e.g., ceramic, at the distal end of the shaft. The insulating member is preferably a tubular structure that separates the active electrode terminal from a tubular or annular return electrode positioned proximal to the insulating member and the active electrode. In another embodiment, the catheter or probe includes a single active electrode that can be rotated relative to the rest of the catheter body, or the entire catheter may be rotated related to the lead. The single active electrode can be positioned adjacent the scar tissue and energized and rotated as appropriate to remove this tissue.

Figure 2:
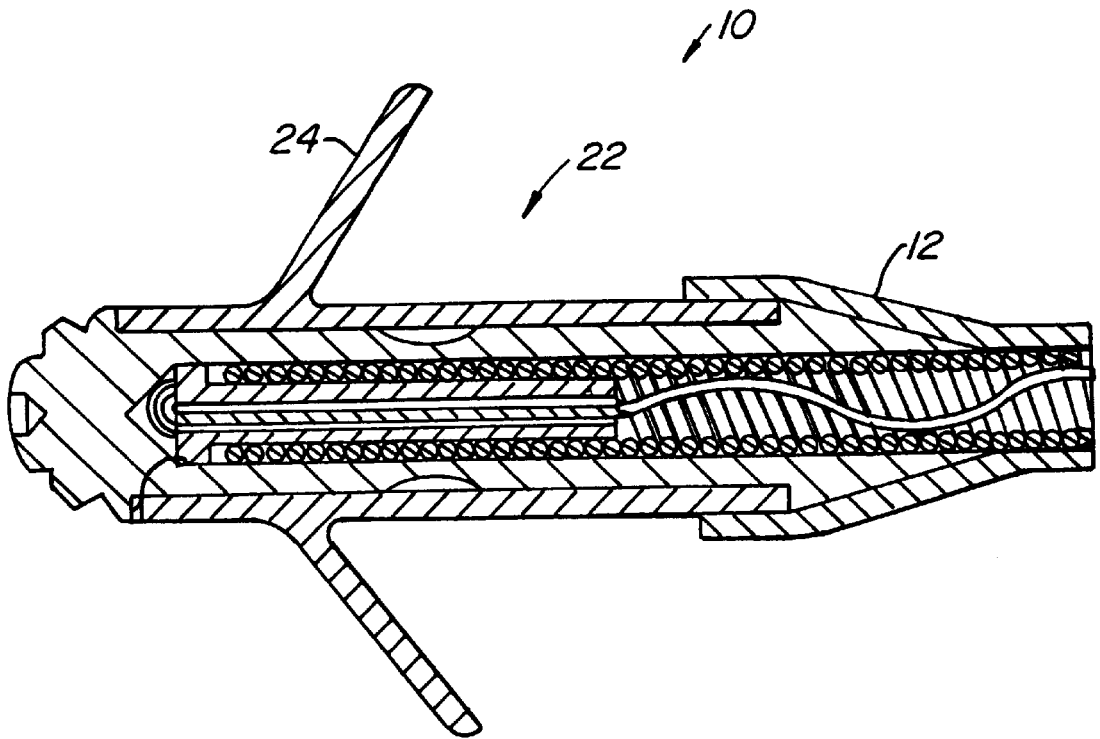
FIG. 2 is an exploded, cross-sectional view of the tip of the pacemaker lead.
Figure 11:
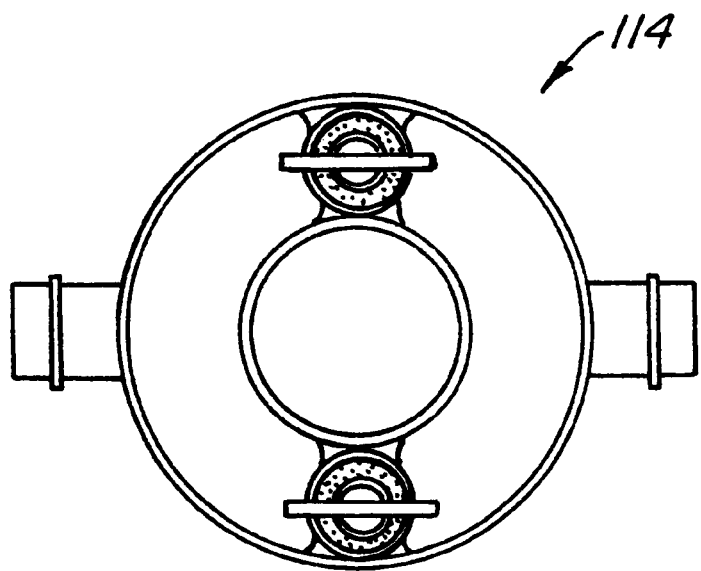
FIG. 11 is a cross-sectional view of the catheter taken along lines 11—11 in FIG. 10.

FIGS. 1 and 2 illustrate a conventional endocardial pacemaker lead 10 according to the present invention. As shown, the lead 10 typically includes a lead shaft 12 with a proximal hub 16 for attachment to a pulse generator (not shown), and a distal tip 22 that is embedded into the myocardium of the heart (see FIGS. 11 and 12). Many conventional lead tips 22 include expanded diameters and/or flaring tines 24 to ensure that the tip remains embedded in the myocardial tissue. These flaring tines 24 may require flared or deflectable electrodes (discussed in detail below) to extend the radius of the tissue cutting/ablation beyond the diameter of the main catheter body.

Figure 3:
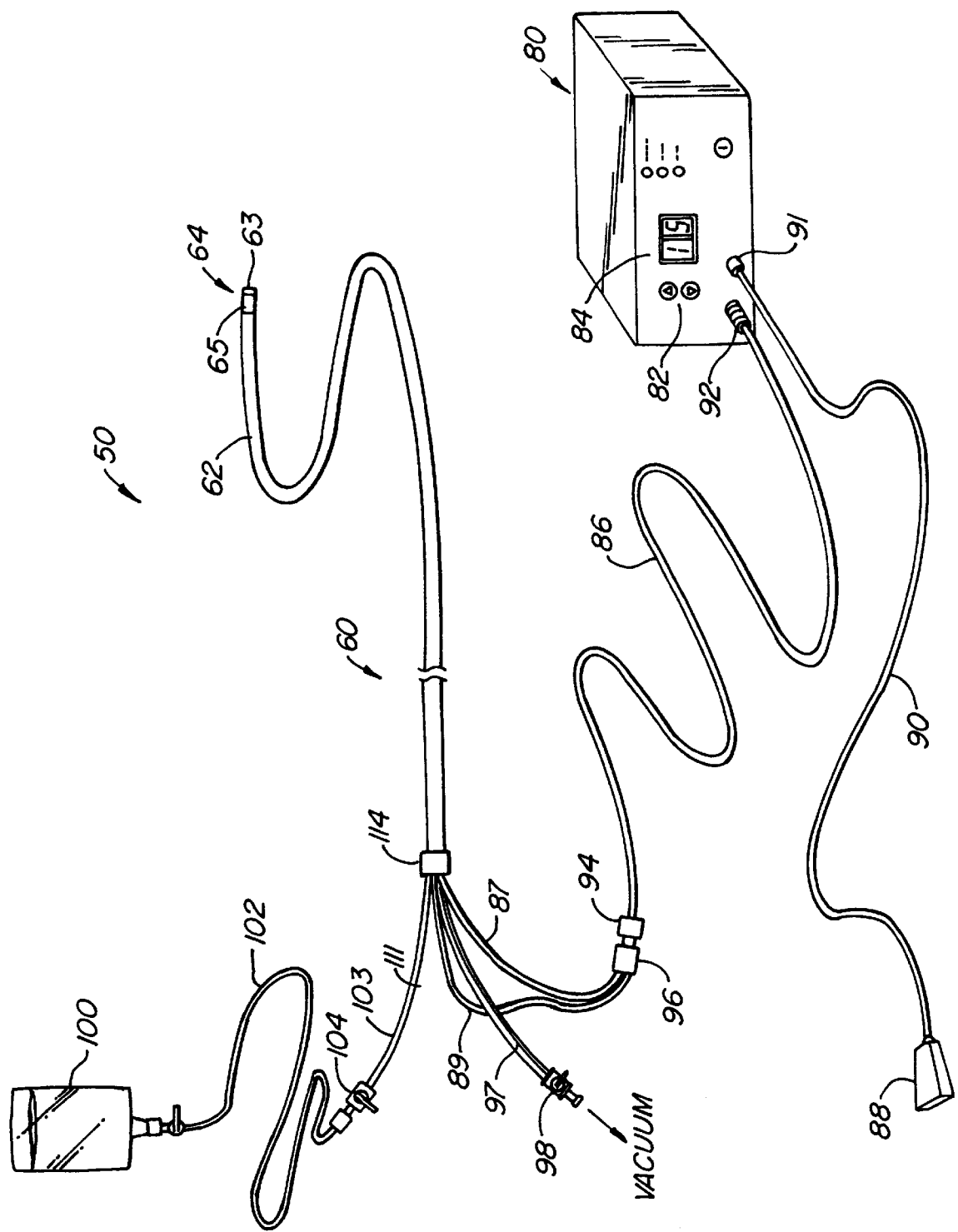
FIG. 3 is a perspective view of an electrosurgical catheter system for removing implanted objects within a patient's body.
Figure 6:
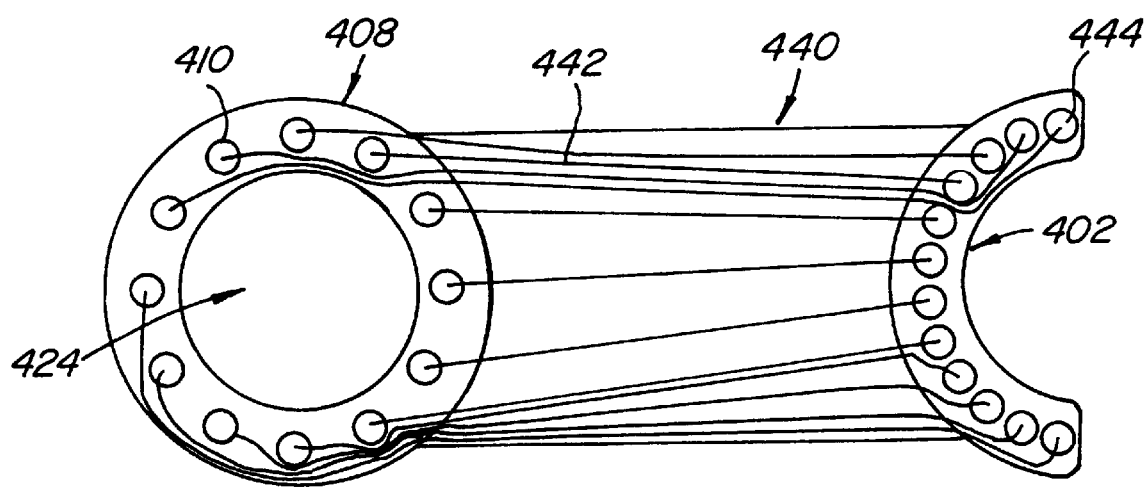
FIGS. 6 and 7 are perspective and cross-sectional views of a flex circuit for coupling a plurality of electrode terminals within the catheter of FIG. 4 to a high frequency power supply.

Referring now to FIG. 3, a catheter system 50 for removing implanted objects from the body, such as pacemaker leads, is illustrated according to the present invention. Catheter system 50 generally comprises an electrosurgical catheter 60 connected to a power supply 80 by an interconnecting cable 86 for providing high frequency voltage to a target tissue and an irrigant reservoir or source 100 for providing electrically conducting fluid to the target site. Catheter 60 generally comprises an elongate, flexible shaft body 62 including a tissue removing or ablating region 64 at the distal end of body 62. The proximal portion of catheter 6 includes a multi-lumen fitment 114 (see also FIGS. 6 and 7) which provides for interconnections between lumens and electrical leads within catheter 60 and conduits and cables proximal to fitment 114. By way of example, a catheter electrical connector 96 is removably connected to a distal cable connector 94 which, in turn, is removably connectable to generator 80 through connector 92. One or more electrically conducting lead wires (not shown) within catheter 60 extend between one or more active electrodes 63 at tissue ablating region 64 and one or more corresponding electrical terminals (also not shown) in catheter connector 96 via active electrode cable branch 87. Similarly, one or more return electrodes 65 at tissue ablating region 64 are coupled to a return electrode cable branch 89 of catheter connector 96 by lead wires (not shown). Of course, a single cable branch 91 may be used for both active and return electrodes, as shown in FIG. 6.

Power supply 80 has an operator controllable voltage level adjustment 82 to change the applied voltage level, which is observable at a voltage level display 84. Power supply 80 also includes a foot pedal 88 and a cable 90 which is removably coupled to power supply 80 for remotely adjusting the energy level applied to electrode terminals. In an exemplary embodiment, power supply 80 includes three such foot pedals (not shown), wherein the first foot pedal is used to place the power supply into the "ablation" mode and the second foot pedal places power supply 80 into the "coagulation" mode. The third foot pedal allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 82 or the third foot pedal may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 80 applies a low enough voltage to the electrode terminals (or the coagulation electrode) to avoid vaporization of the electrically conductive fluid and subsequent molecular dissociation of the tissue. The surgeon may automatically toggle the power supply between the ablation and coagulation modes by alternatively stepping on the foot pedals. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on the appropriate foot pedal, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on a foot pedal. A specific design of a suitable power supply for use with the present invention can be found in provisional patent application entitled "SYSTEMS AND METHODS FOR ELECTROSURGICAL TISSUE AND FLUID COAGULATION", Ser. No. 60/062,997 filed Oct. 23, 1997, previously incorporated herein by reference.

Conductive fluid 30 is provided to tissue ablation region 64 of catheter 60 via an internal lumen 68 (see FIG. 5) within catheter 60. Fluid is supplied to the lumen from the source along a conductive fluid supply line 102 and a conduit 103, which is coupled to the inner catheter lumen at multi-lumen fitment 114. The source of conductive fluid (e.g., isotonic saline) may be an irrigant pump system (not shown) or a simple gravity-driven supply, such as an irrigant reservoir 100 positioned several feet above the level of the patient and tissue ablating region 64. A control valve 104 may be positioned at the interface of fluid supply line 102 and conduit 103 to allow manual control of the flow rate of electrically conductive fluid 30. Alternatively, a metering pump or flow regulator may be used to precisely control the flow rate of the conductive fluid.

Catheter system 50 further includes an aspiration or vacuum system (not shown) to aspirate liquids and gases from the target. One or more internal suction lumens 130, 132 within catheter body 62 are suitably coupled to a fluid tube 97 at the proximal end of catheter 60. Fluid tube 97, in turn, includes a connector 98 for coupling to a controllable source of vacuum (not shown).

Figure 9:
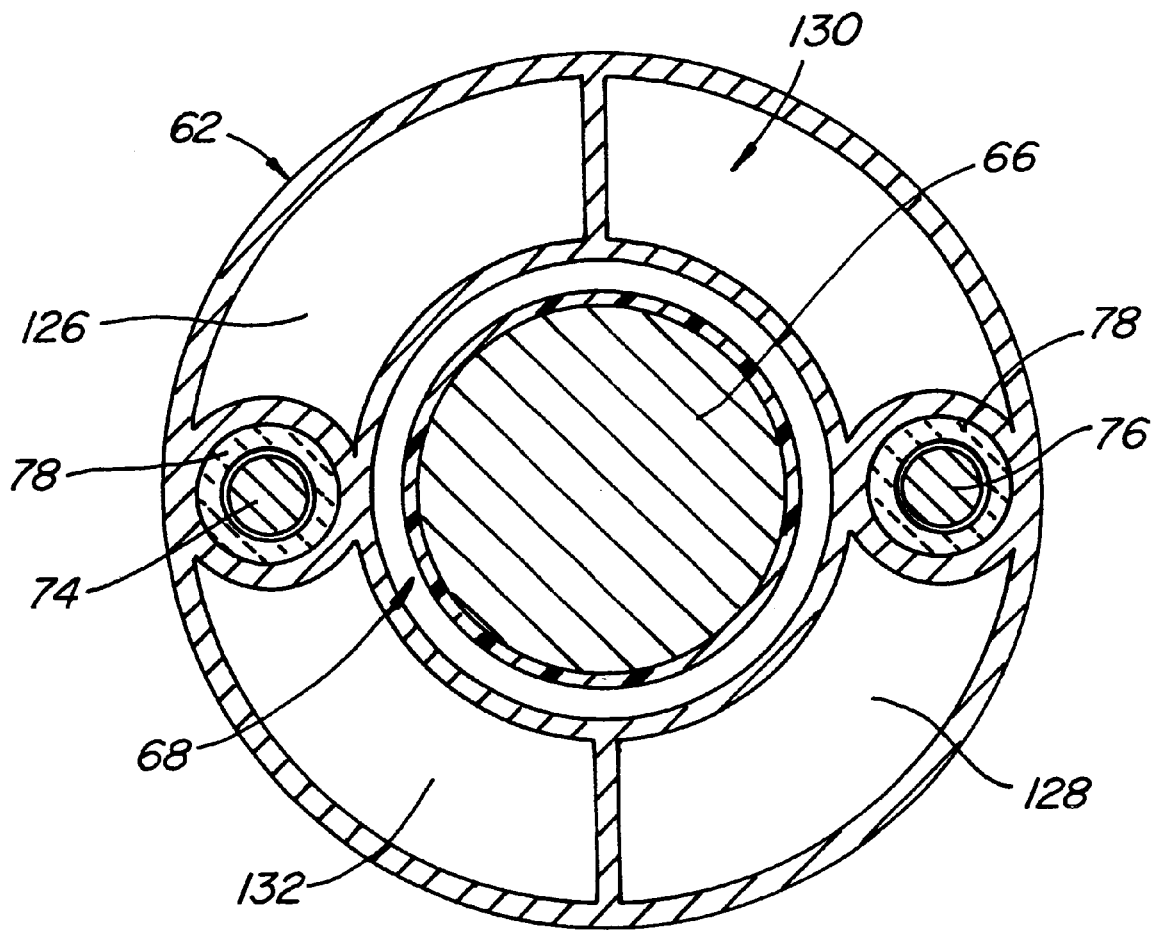
FIG. 9 is a cross sectional view of the electrosurgical catheter taken along lines 9—9 in FIG. 8A.
Figure 10:
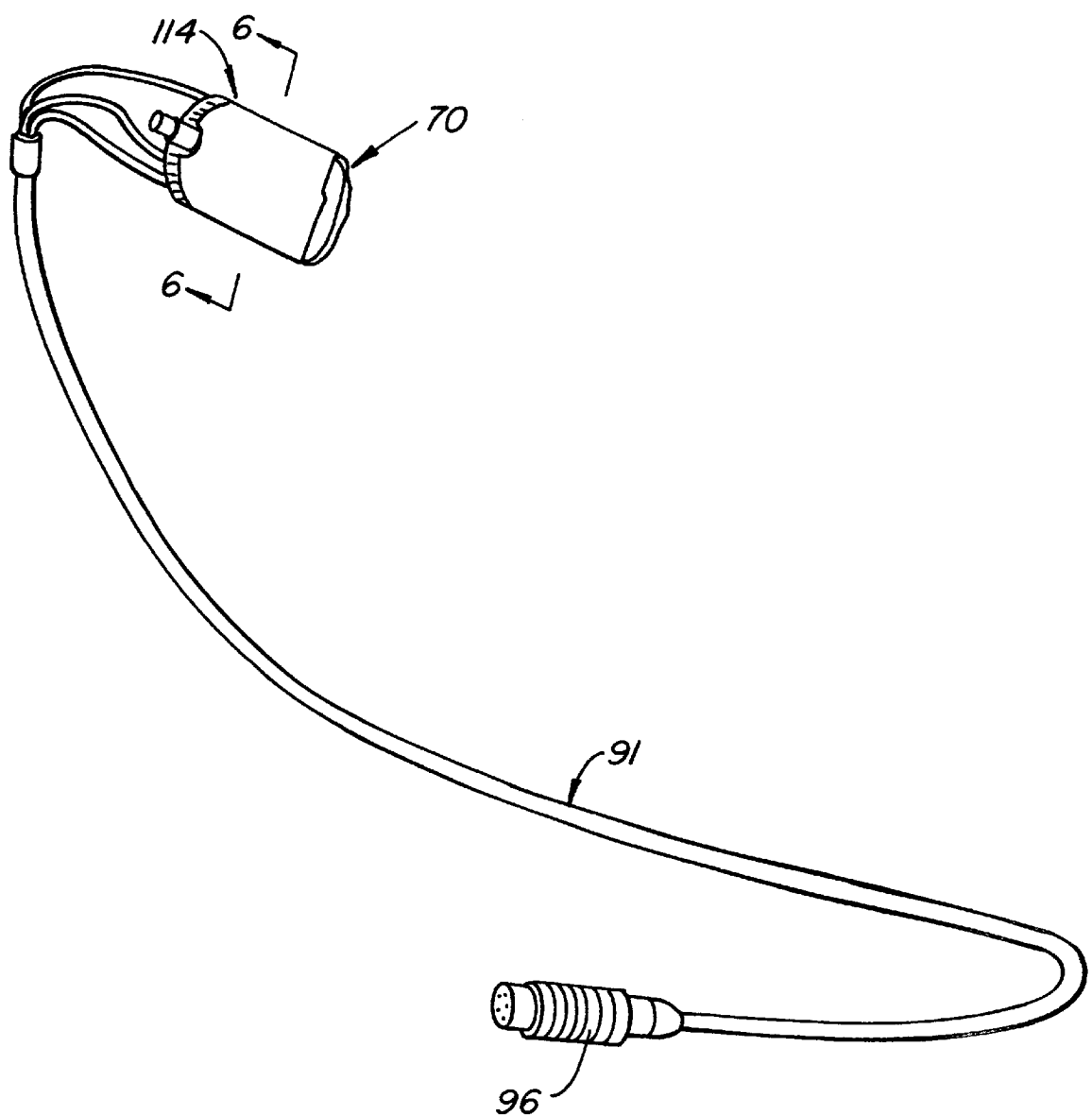
FIG. 10 illustrates the proximal portion of the electrosurgical catheter of FIG. 8A.

Referring now to FIGS. 4–7, one embodiment of a catheter 400 according to the present invention will now be described. As shown in FIG. 4, catheter 400 includes a flexible catheter body 402 coupling a proximal handle 404 to a distal ablation region 406. Distal ablation region 406 includes an electrode support member 408 which provides support for a plurality of electrically isolated electrode terminals 410 (see FIG. 5). As shown, support member 408 includes a central lumen 424 for accommodating a pacemaker lead 66 (see FIG. 9) so that the lead 66 only passes through support member 408 (i.e., the entire catheter shaft 402 does not have to be advanced over the lead 66). This design should facilitate the advancement of the catheter 60 over the lead.

In the embodiment shown in FIGS. 4–7, catheter 60 includes a single return electrode 422 for completing the current path between electrode terminals 410 and high frequency power supply 80 (see FIG. 3). As shown, return electrode 422 preferably comprises an annular conductive band coupled to the distal end of shaft 402 slightly proximal electrode support member 408, typically about 0.5 to 20 mm and more preferably about 1 to 10 mm. Return electrode 422 is coupled to a connector (not shown) that extends to handle 404, where it is suitably connected to power supply 80, as discussed above.

As shown in FIG. 4, return electrode 422 is not directly connected to electrode terminals 410. To complete this current path so that electrode terminals 410 are electrically connected to return electrode 422, electrically conducting fluid (e.g., isotonic saline, electrically conductive gel, or an electrically conductive gas) is caused to flow therebetween. In the representative embodiment, the electrically conducting fluid is delivered through a fluid tube 412 to an opening at the distal end 420 of catheter shaft 402. Fluid tube 412 extends through an opening in handle 404, and includes a connector 414 for connection to a fluid supply source, for supplying electrically conductive fluid to the target site. Depending on the configuration of the distal ablation region 406, fluid tube 412 may extend through a single lumen (not shown) in shaft 401, or it may be coupled to a plurality of lumens (also not shown) that extend through shaft 402. In the representative embodiment, the fluid lumen(s) have openings (not shown) at the distal end 420 of the catheter shaft 402 to discharge the electrically conductive fluid proximal to return electrode 422 and electrode terminals 410. However, the lumens may extends through to support member 408, if desired. Catheter 400 may also include a valve (not shown) or equivalent structure for controlling the flow rate of the electrically conducting fluid to the target site.

In alternative embodiments, the fluid path may be formed in catheter 400 by, for example, an inner lumen or an annular gap between the return electrode and a tubular support member within shaft 402. This annular gap may be formed near the perimeter of the shaft 402 such that the electrically conducting fluid tends to flow radially inward towards the target site, or it may be formed towards the center of shaft 402 so that the fluid flows radially outward. In other embodiments, the fluid may be delivered by a fluid delivery element (not shown) that is separate from catheter 60. A more complete description of an electrosurgical instrument incorporating one or more fluid lumen(s) can be found in parent application Ser. No. 08/485,219, filed on Jun. 7, 1995, the complete disclosure of which has previously been incorporated herein by reference.

Referring to FIG. 5, the electrically isolated electrode terminals 410 are spaced apart over a distal tissue treatment surface 430 of electrode support member 408. The tissue treatment surface 430 and individual electrode terminals 410 will usually have dimensions within the ranges set forth above. In the representative embodiment, the tissue treatment surface 430 has an circular cross-sectional shape with a diameter in the range of 1 mm to 20 mm, preferably about 1 to 5 mm. The individual electrode terminals 410 preferably extend outward from tissue treatment surface 430 by a distance of about 0.05 to 4 mm, usually about 0.1 to 1 mm.

In the embodiment of FIGS. 4–7, the catheter includes a single, larger opening 424 in the center of tissue treatment surface 430, and a plurality of electrode terminals (e.g., about 3–30) around the perimeter of surface 430. Alternatively, the catheter 60 may include a single, annular, or partially annular, electrode terminal at the perimeter of the tissue treatment surface. The central lumen 424 (or a peripheral lumen) may be coupled to a suction lumen (not shown) within shaft 402 for aspirating tissue, fluids and/or gases from the target site. Aspirating the electrically conductive fluid during surgery allows the surgeon to see the target site, and it prevents the fluid from flowing into the patient's body, e.g., into the heart or lung.

Handle 404 typically comprises a plastic material that is easily molded into a suitable shape for handling by the surgeon. Handle 404 defines an inner cavity that houses the electrical connections (not shown), and provides a suitable interface for connection to an electrical connecting cable (see FIG. 1). A more complete description of an exemplary handle and associated electrical connections can be found in co-pending U.S. Patent Application entitled "Systems and Methods for Endoscopic Sinus Surgery", filed Dec. 15, 1997, the complete disclosure of which is incorporated herein by reference.

Figure 7:
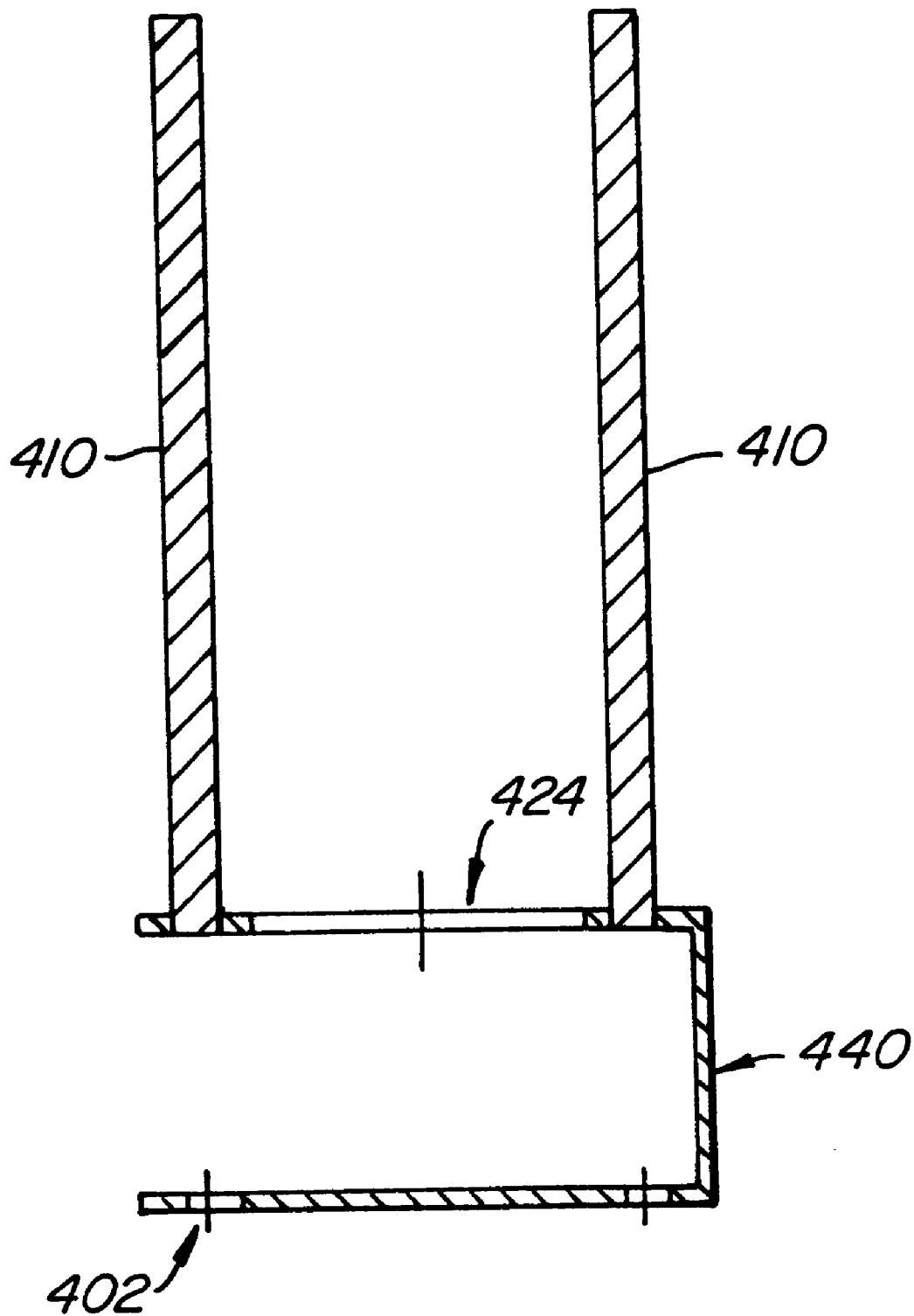

Referring now to FIGS. 6 and 7, an exemplary flex circuit 440 for electrically coupling electrode terminals 410 to the catheter body 402 will now be described. As shown, flex circuit 440 includes a plurality of flexible wires 442 (e.g., copper wires) coupling electrode terminals 410 to a plurality of connectors 444 on catheter shaft 402, which are suitably coupled to wires or other electrical connectors that extend through shaft 402 to handle 404. Flex circuit 440 preferably comprises a flexible material, such as polymide, that can be deformed such that wires 442 extend from each of the electrode terminals 410 surrounding lumen 424 of support member 408 to one side of support member 408, and then back to a semi-circular configuration within catheter shaft 408. This design ensures that the wires 442 do not interfere with the pacemaker lead 66 (FIG. 9) that extends through lumen 424 as the support member 408 is advanced over the lead.

Of course, it should be recognized that other configurations are possible. For example, the catheter shaft 402 may have the same or a larger diameter as support member 408 so that central lumen 424 of support member 408 abuts against the catheter shaft 402. In this configuration, shaft 402 will have also have a central lumen aligned with lumen 424 for accommodating the pacemaker lead through a portion or all of the shaft. In one embodiment (see FIG. 15), for example, the catheter shaft 402 may have a slit or opening disposed proximal to support member 408 that allows pacemaker lead to be fed through the slit and the internal lumen, similar to the embodiment described above. In this embodiment, a flex circuit may not be desirable or necessary.

Figure 8A:
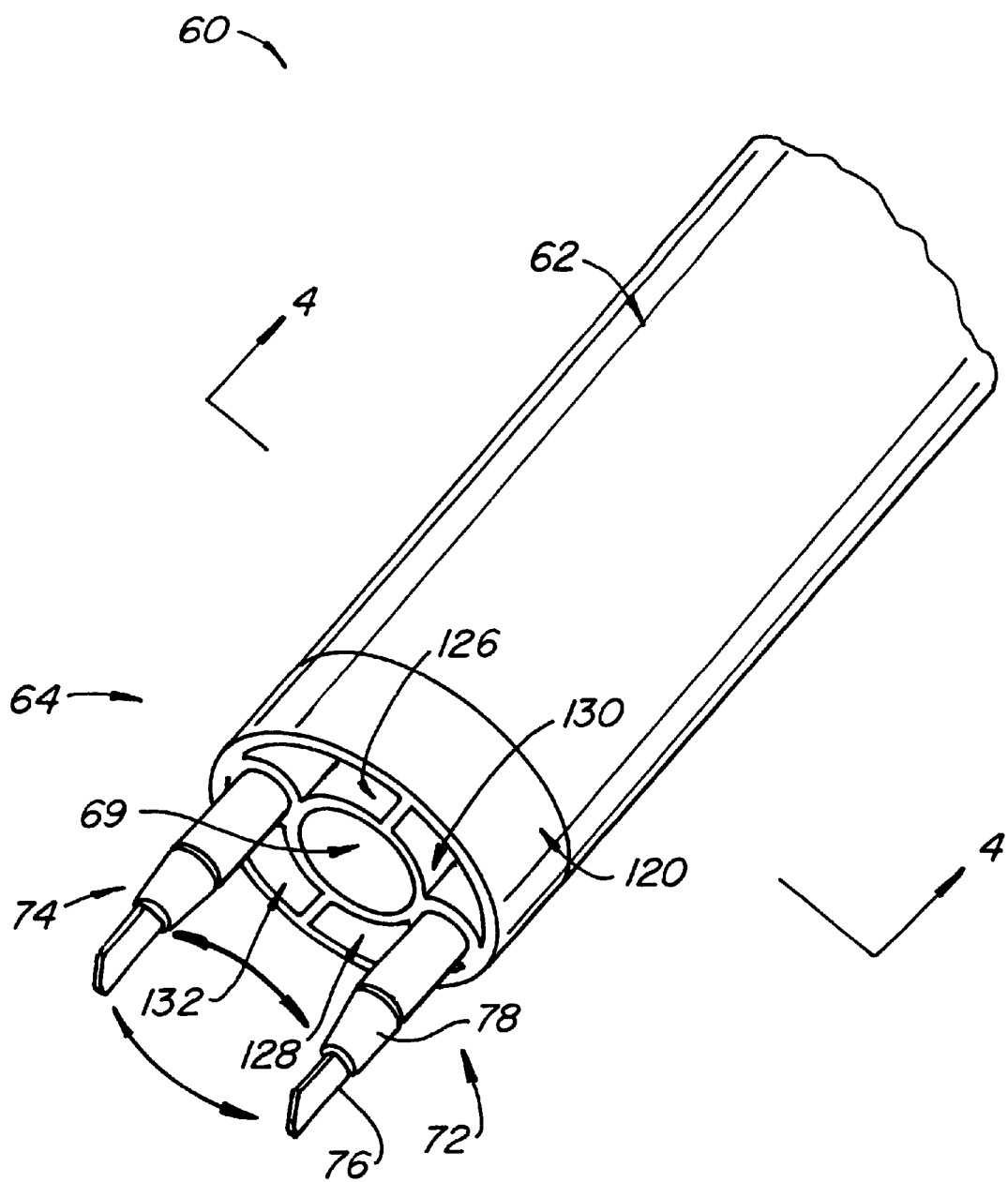
FIG. 8A is a perspective view of a distal portion of a second embodiment of an electrosurgical catheter according to the present invention.

Referring not to FIGS. 8–12, a second embodiment of a catheter according to the present invention will now be described. As shown in FIG. 8, catheter body 62 has an internal lumen 68 sized to accommodate a pacemaker lead 66 (see FIG. 9), as described above. In this embodiment, internal lumen 68 extends from a distal opening 69 (see FIG. 8A) to the proximal end 70 of catheter body 62 (FIG. 10) so that the pacemaker lead 66 acts as the guidewire for advancing the distal end of the catheter to the target site. Of course, a separate guidewire (not shown) may be used to guide distal ablation region 64 of catheter 60 to the target site. In particular, for other applications, such as removing tissue ingrown around a the distal end of catheter 60 to the stent. For the removal of pacemaker leads, however, applicant has found that it is advantageous to use the lead as the guidewire because the distal end of catheter 60 is already positioned to remove the fibrous scar tissue between the heart wall and the lead.

As shown in FIG. 8A, the distal ablation region 64 of catheter body 62 includes first and second electrode assemblies 72, 74 extending beyond the distal opening 69 of the central lumen 68. Of course, it will be recognized that the catheter may include more or less than two electrode assemblies (e.g., see FIGS. 16–21). Electrode assemblies 72, 74 stent or stent-graft within a body lumen, for example, a guidewire may be utilized to guide each include an active electrode terminal 76 extending from an electrically insulating support member 78. Electrode terminals 76 preferably comprise an electrically conductive metal or alloy, such as platinum, titanium, tantalum, tungsten, stainless steel, gold, copper, nickel and the like. The electrode terminals 76 should be sufficiently long to extend the "coring" depth of the terminals 76 during the ablation/cutting operation to at least 0.5 mm, usually at least 2 mm, preferably at least 5 mm.

In addition, electrode terminals 76 preferably an active portion or surface having a surface geometry shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface (s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a PH less than 7.0 or by using a high velocity stream of abrasive particles (e.g., grit blasting) to create asperities on the surface of an elongated electrode. A more complete description of suitable electrode geometries can be found in U.S. application Ser. No. 08/687,792, filed on Jul. 18, 1996, previously incorporated herein by reference.

Figure 12:
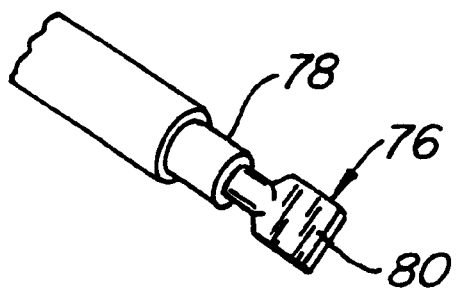
FIG. 12 illustrates one of the electrode assemblies of the electrosurgical catheter according to the embodiment of FIG. 8B.

In the representative embodiment, electrode terminals 76 preferably comprise electrode wires which are flattened at their tips 80 (e.g., in the shape of a screwdriver tip) to provide a more rapid tissue ablation/cutting action (see FIG. 12). The support members 78 comprise an inorganic insulator, such as ceramic, glass, glass/ceramic or a high resistivity material, such as silicon or the like. An inorganic material is generally preferred for the construction of the support members 78 since organic or silicone based polymers are known to rapidly erode during sustained periods of the application of high voltages between electrodes terminals 76 and the return electrode 120 during tissue ablation. However, for situations in which the total cumulative time of applied power is less than about one minute, organic or silicone based polymers may be used without significant erosion and loss of material of the support members 78 and, therefore, without significant reduction in ablation performance.

In the embodiment shown in FIG. 8A, catheter 60 includes a single return electrode 120 for completing the current path between electrode terminals 76 and power supply 80 (see FIG. 3). As shown, return electrode 120 preferably comprises an annular conductive band at the distal end of catheter 60 slightly proximal to electrode support members. Return electrode 90 is spaced from electrode terminals 76 a sufficient distance from the electrode terminals 76 to substantially avoid or minimize current shorting therebetween and to shield the return electrode 120 from tissue at the target site, usually about 0.5 to 10 mm and more preferably about 1 to 10 mm. Return electrode 120 is coupled to a connector (not shown) that extends to the proximal end of catheter 60, where it is suitably connected to power supply 80 by connector 89, as described above in connection with FIG. 3.

Figure 8B:
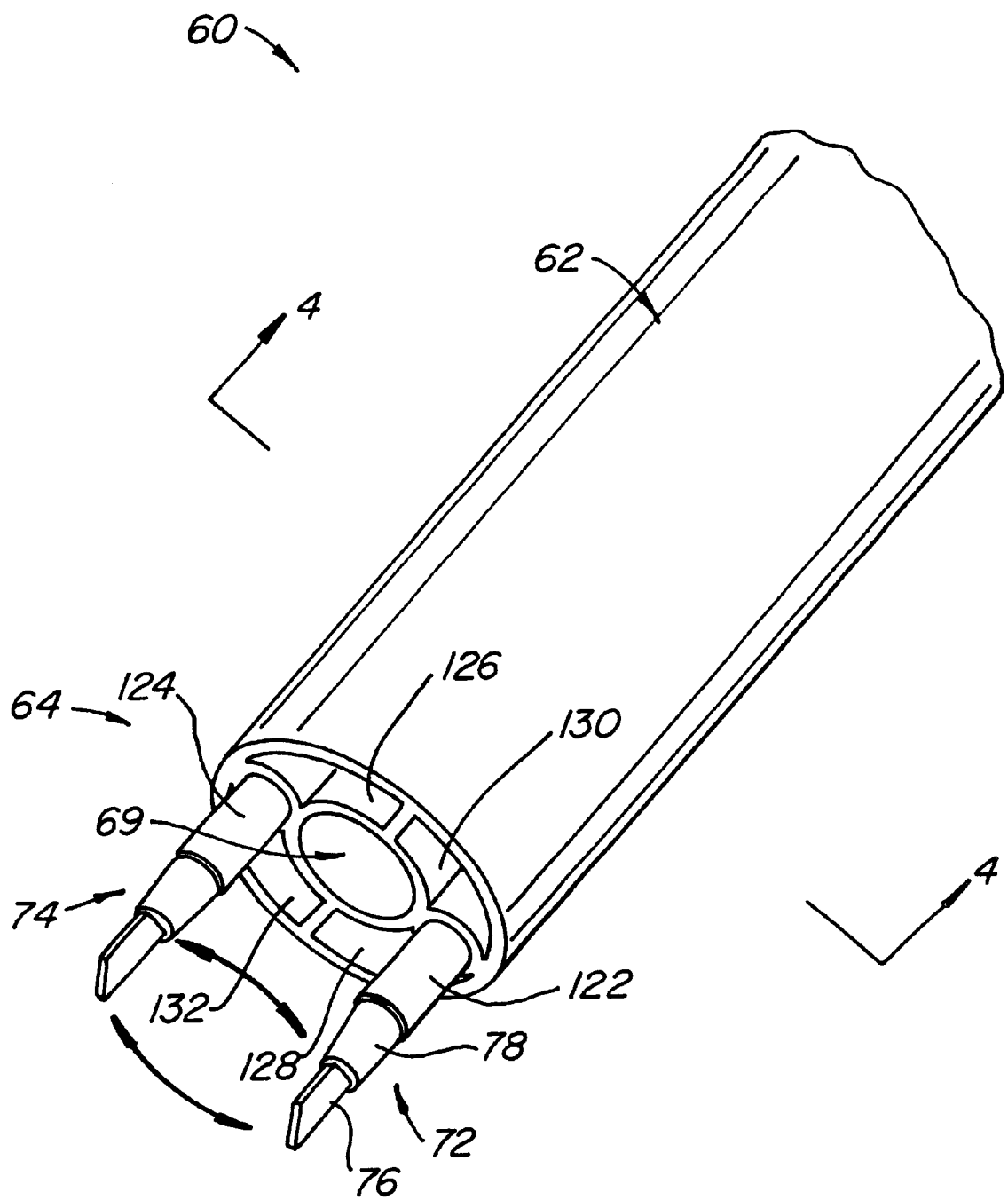
FIG. 8B illustrates a third embodiment of the catheter, incorporating a pair of return electrodes.

In the embodiment shown in FIG. 8B, catheter 60 includes a pair of return electrodes 122, 124 located on electrode assemblies 72, 74 proximal to the support members 78. As in the above embodiment, return electrodes 122, 124 are spaced from electrode terminals 76 a sufficient distance to substantially avoid or minimize current shorting therebetween and to shield the return electrodes 122, 124 from tissue at the target site. This embodiment has the advantage that the electric currents are substantially confined to a region that is distal to the distal end of catheter body 62, which facilitates advancement of the catheter body 60 through fibrous scar tissue.

Both embodiments (FIGS. 8A and 8B) include a pair of fluid lumens 126, 128 for delivering electrically conductive fluid, e.g., isotonic saline or argon gas, to the electrode terminals 76, and a pair of suction lumens 130, 132 for aspirating fluids and/or tissue fragments from the target site. The fluid lumens 126, 128 extend through catheter body 62 to fluid tube 103 (see FIG. 3). The electrically conductive fluid provides a current flow path between electrode terminals 76 and the return electrodes 120, 122, 124. In addition, the fluid is one of the requisites for establishing the Coblation™ mechanism of the present invention, as discussed above. Alternatively or additionally, the body's naturally conductive fluids (e.g., blood) may be used for these purposes depending on the location of the implanted object (e.g., a stent located within a blood vessel). The suction lumens 130, 132 also extend through catheter body 62 to a source of vacuum (not shown) for aspirating gaseous products of ablation and/or tissue fragments from the target site. In addition, the suction lumens 130, 132 may be used to aspirate excess electrically conductive fluid from the target site, if, for example, a high flow rate of this fluid is necessary for the procedure.

Catheter body 62 preferably includes reinforcing fibers or braids (not shown) in the walls of at least the distal ablation region 64 of body 62 to provide responsive torque control for rotation of electrode terminals 76 during tissue engagement. This rigid portion of the catheter body 62 preferably extends only about 7 to 10 mm while the remainder of the catheter body 62 is flexible to provide good trackability during advancement and positioning of the electrodes 74, 76 adjacent to the pacemaker lead 66.

Figure 13:
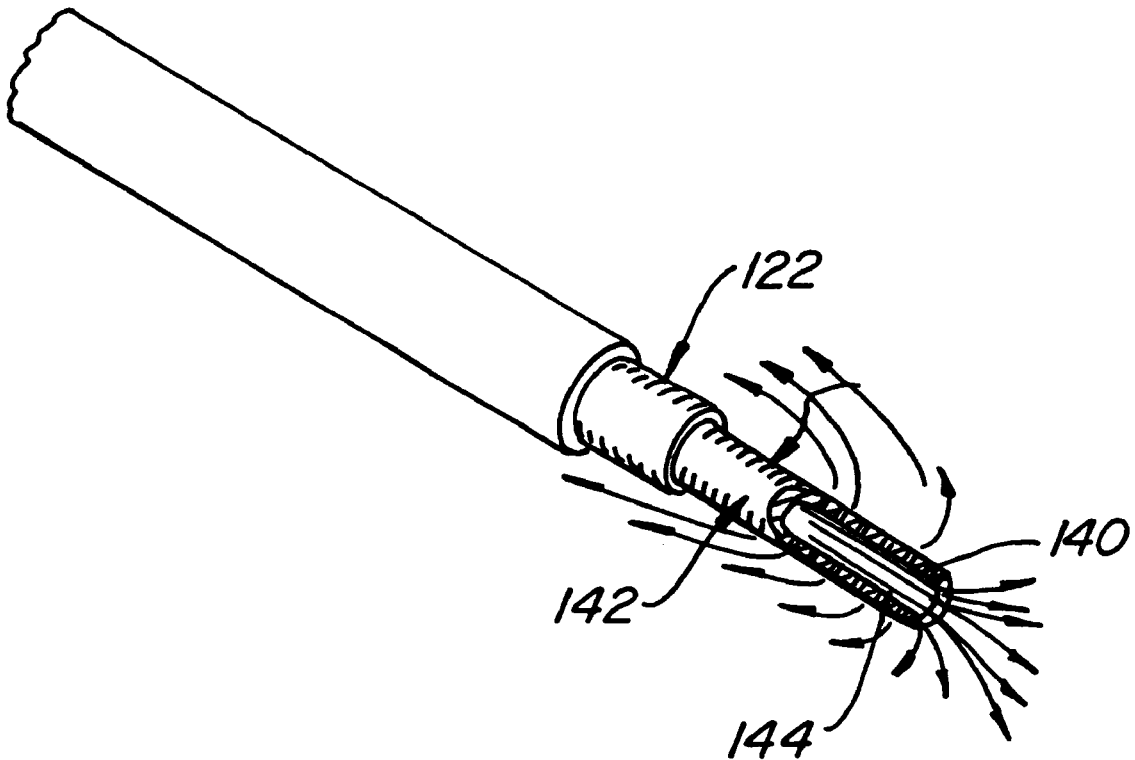
FIG. 13 illustrates an alternative embodiment of an electrode assembly incorporating a central fluid lumen for delivery of electrically conductive fluid to the target site.

As an alternative to the irrigation lumens shown in FIGS. 8–12, the irrigant or electrically conductive fluid may be supplied through the lumen 140 of tubular electrodes 142 (see FIG. 13) in place of the shaped, solid wires shown in FIGS. 8–12. This may be advantageous in ensuring that electrically conductive fluid is injected into close proximity to the site of tissue ablation/cutting. Further, the tubing can be filed as shown in FIG. 13 to expose additional edges 144 to enhance the tissue cutting effect.

Figure 14A:
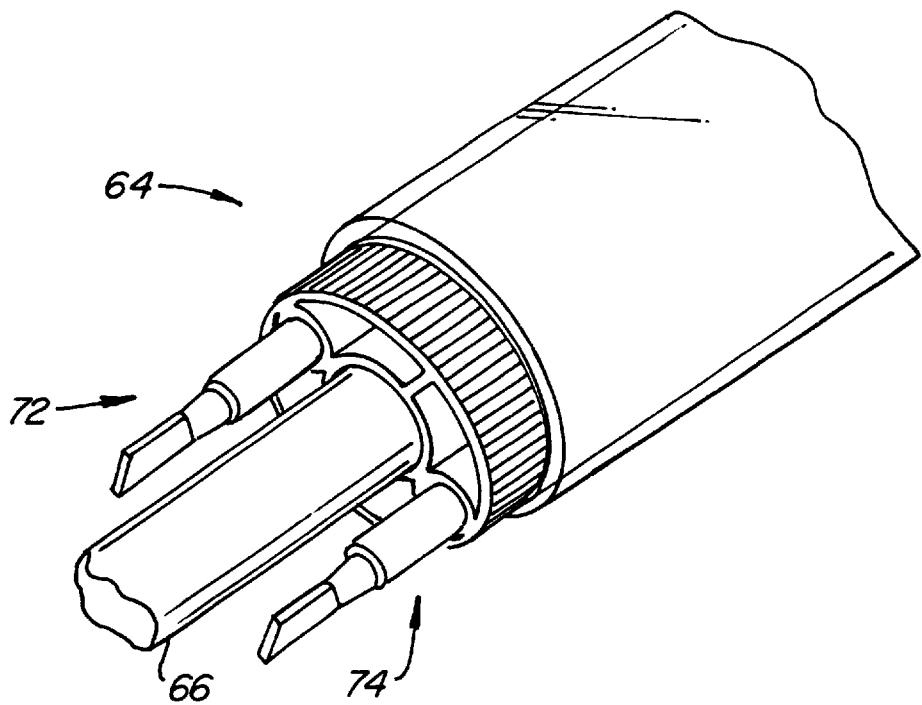
FIGS. 14A and 14B illustrates a fourth embodiment of an electrosurgical catheter incorporating a retractable safety sheath for shielding the patient from the electrode assemblies.
Figure 14B:
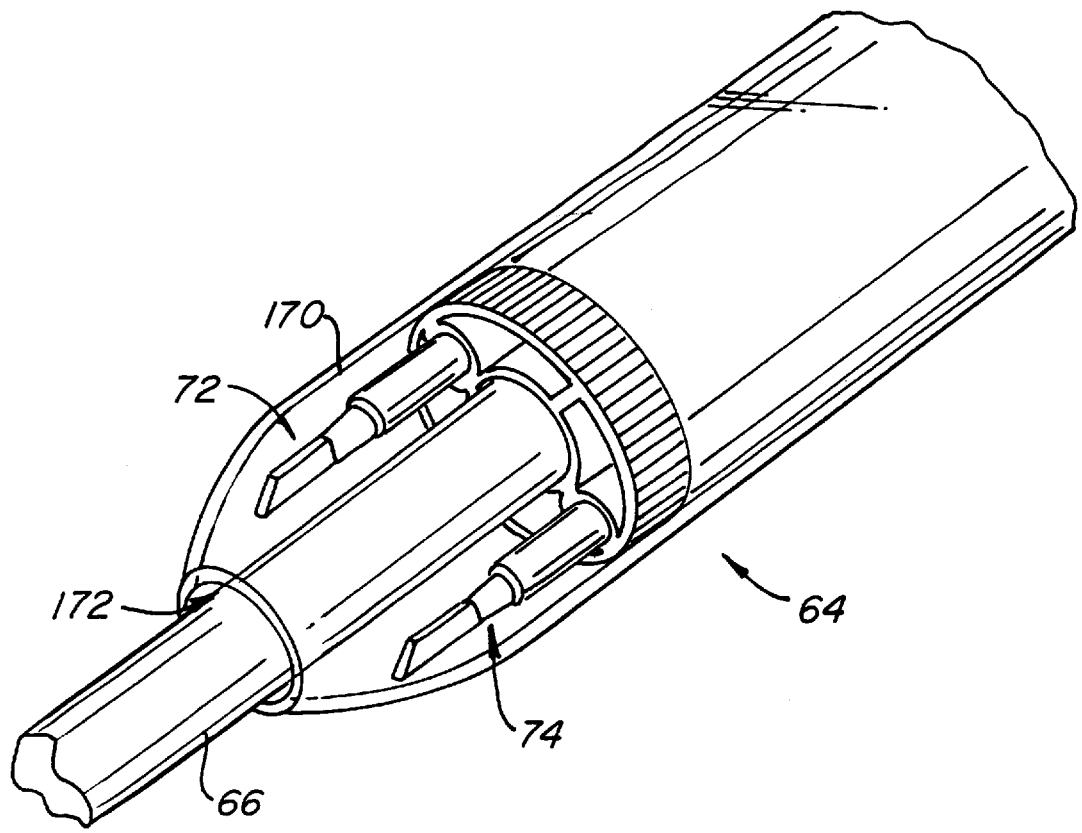

During the percutaneous introduction and removal of catheter body 62, measures should be taken to prevent iatrogenic injury to the walls of the vessels and heart as well as the valves and other tissues encountered along the pathway to the target site, viz., the embedded portion of the pacemaker lead tip. In the embodiment shown in FIGS. 14A and 14B, catheter 60 includes a compliant, atraumatic safety sheath 170 which extends over electrode assemblies 72, 74. Safety sheath 170 has a distal opening 172 for accommodating lead 66, and comprises a compliant material that will allow sheath to retract over catheter body 64, as shown in FIG. 14A. In use, sheath 170 is advanced forward as shown in FIG. 14A during introduction and removal of tissue ablation region 64. Once the target site has been accessed, the compliant, atraumatic safety sheath 170 is retracted (e.g., a distance of 1.5 to 2.0 cm) exposing electrode assemblies 72, 74. Once the ablation of an annular channel in the tissue surrounding the pacemaker lead tip 66 is complete, the safety sheath 170 can be displaced forward to cover the distal portion of ablation region 64.

The safety sheath 170 is preferably constructed using thin-walled plastic tubing selected to provide biocompatability, compliance and low friction during insertion and removal. A number of plastic materials are available for this purpose and include Teflon, polypropylene and polyvinyl chloride. The activation mechanism may be (1) the thin-walled plastic tubing moved relative to the catheter body at a location external to the patient's body or (2) a drive rod or wire (not shown) within the catheter body which actuates a short segment of the safety sheath (e.g., 4 to 8 cm) located at the distal end of the catheter body.

Figure 15:
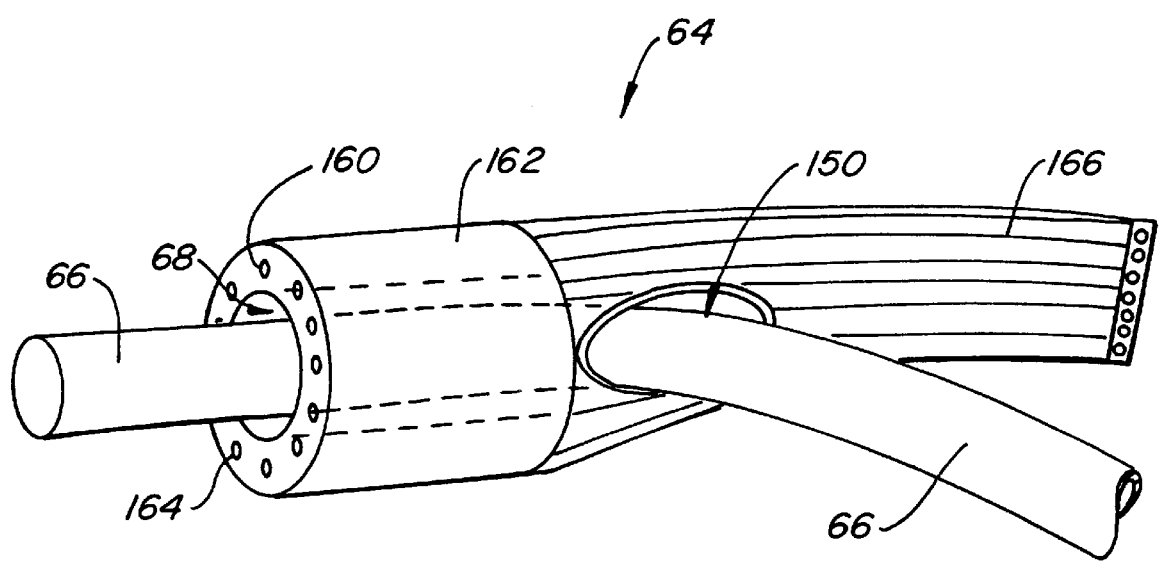
FIG. 15 illustrates a fifth embodiment of an electrosurgical catheter incorporating a lateral port for loading a pacemaker lead.

Another embodiment of the present invention is shown in FIG. 15. In this embodiment, catheter body 62 includes a lateral or side port 150 at or near tissue ablation region 64. As shown, lateral port 150 is coupled to central lumen 68, and allows the distal end portion of the catheter 60 to be advanced over the pacemaker lead 66 without having to extend the lead 66 through the entire length of the catheter 60. This facilitates the procedure and typically shortens the amount of time required to advance electrode terminals 160 along the lead 66. The side port 150 may be formed in the catheter body 62 proximal to electrically insulating member 162 as shown in FIG. 15, or it may be formed directly in the insulating member 162.

In the embodiment of FIG. 15, electrode terminals 160 are spaced around the periphery of a ceramic insulating support member 162. In addition, support member 162 may include one or more holes 164 for delivering of electrically conductive fluid and/or for aspirating the target site. Alternatively, aspiration and/or fluid delivery may be accomplished through central lumen 68. As shown in FIG. 15, electrode terminals 76 are substantially flush with the distal surface of support member 162. This configuration minimizes the current flux density around the electrode terminals 160 because they have no sharp edges or corners, thereby reducing the rate of tissue ablation. In some cases, applicant has found that this allows a slower and more controlled rate of tissue removal. For fibrous scar tissue around pacemaker leads, however, the sharper, exposed electrode terminals 76 of previous embodiments may be preferred. As shown, electrode terminals 160 each have a flat tape wire 166 that extends through insulating support member 162, and through catheter body 62 to the proximal end thereof.

Figure 16A:
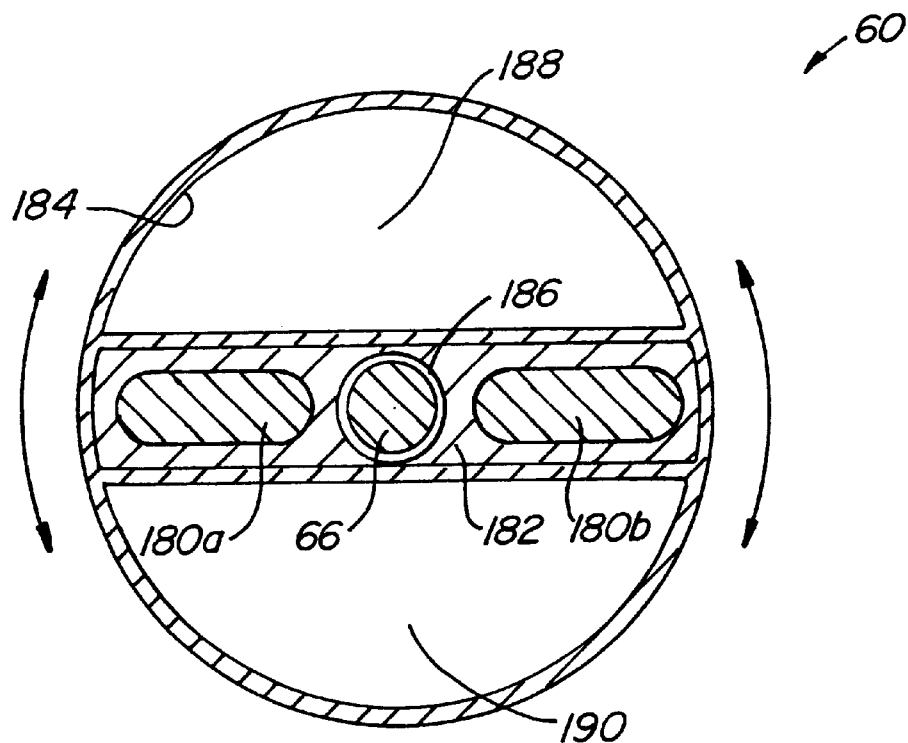
FIGS. 16A and 16B are transverse and longitudinal cross-sectional views, respectively, of a sixth embodiment of the distal ablation region of the catheter.
Figure 16B:
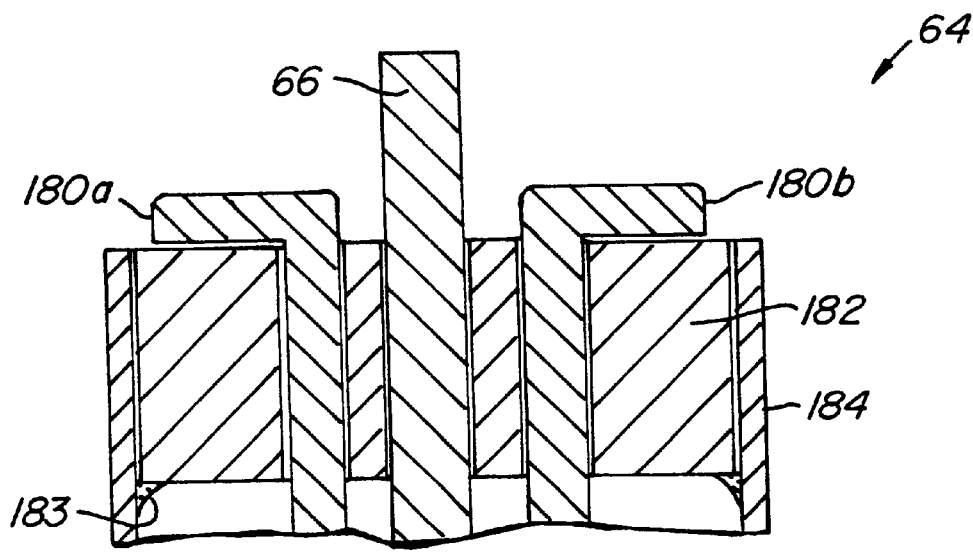
Figure 17A:
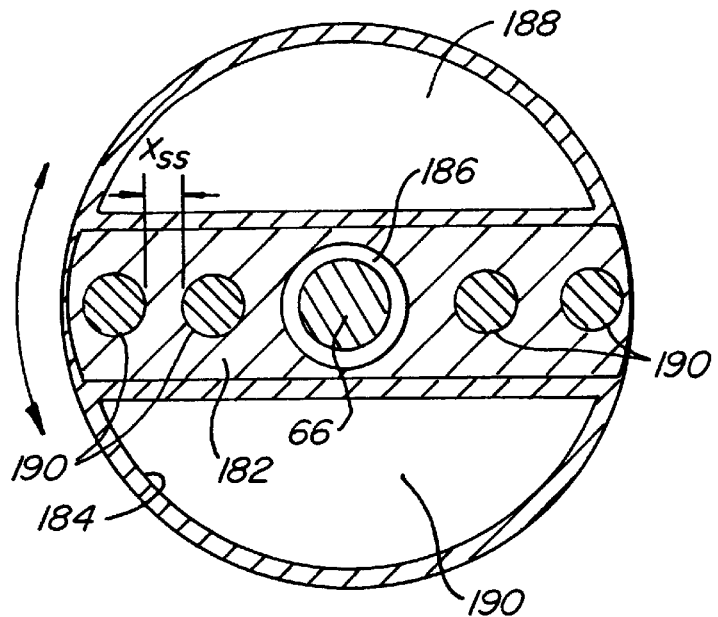
FIGS. 17A and 17B are transverse and longitudinal cross-sectional views, respectively, of a seventh embodiment of the distal ablation region of the catheter.
Figure 17B:
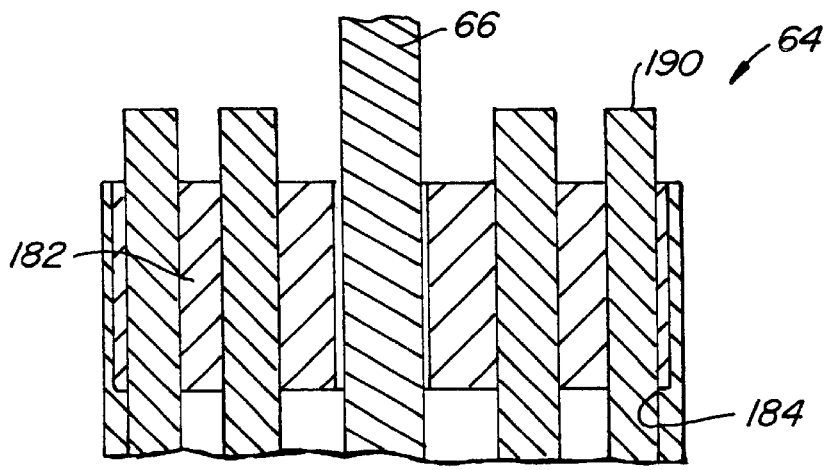
Figure 18A:
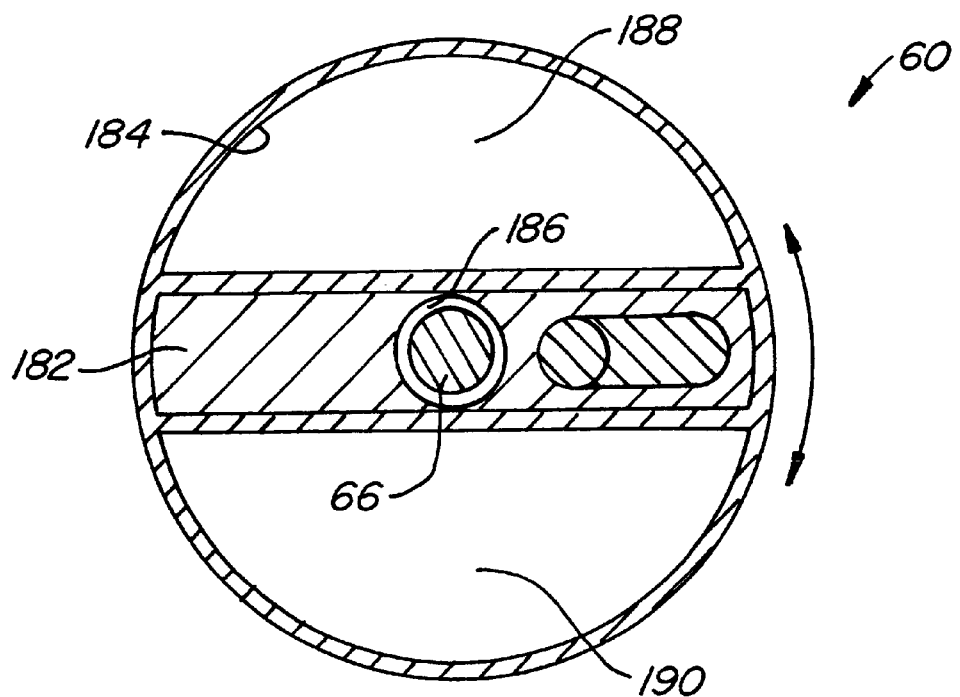
FIGS. 18A and 18B are transverse and longitudinal cross-sectional views, respectively, of an eighth embodiment of the distal ablation region of the catheter.
Figure 18B:
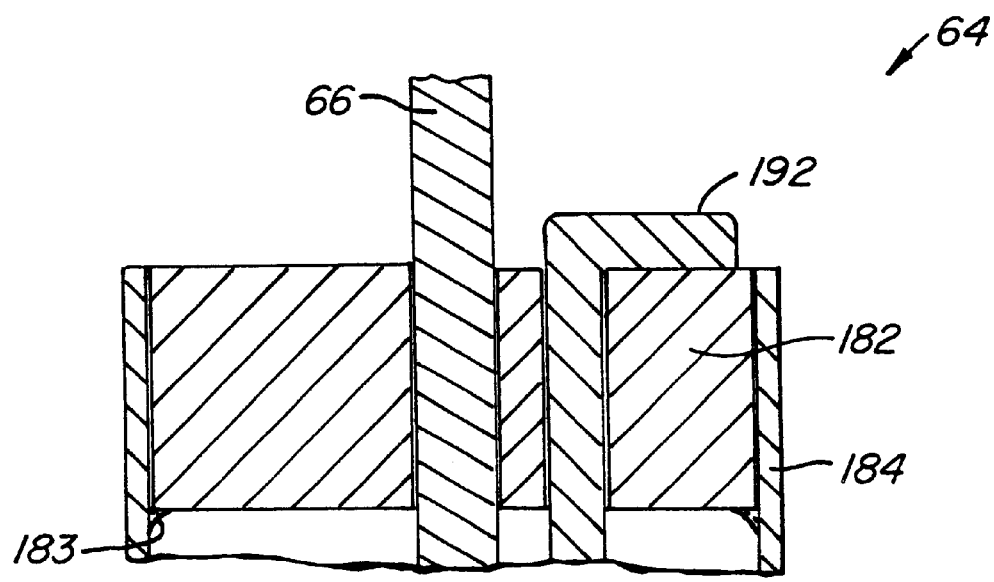

Another embodiment of tissue ablation region 64 of catheter 60 is shown in FIGS. 16A and 16B. As shown, two active electrodes 180a, 180b are secured within an electrically insulating support member 182. The support member 182 is secured to the distal end of catheter 60 with a biocompatible adhesive 183 between support member 182 and outer sleeve 184 of catheter 60. A central lumen 186 in support member 182 provides a passageway for pacemaker lead 66 that permits axial displacement and rotation of tissue ablating region 64 relative to lead 66. An irrigation lumen 188 and an aspiration lumen 190 are also provided to inject electrically conducting fluid and to remove gaseous products of ablation from the target site.

The return electrode (not shown) comprises an annular electrode on the catheter body proximal to support member 182. Alternatively, the return electrode may be located within central lumen 186 proximal of the exposed portion of active electrodes 180a, 180b. In this embodiment, the electric currents are confined to a region between active electrodes 180a, 180b and central lumen 186, which may further limit current penetration into the surrounding heart wall.

In use with the present invention, catheter 60 is rotated as the electrodes 180a, 180b are energized by generator 80 (FIG. 3) to effect ablation of the tissue attached to lead 66. Preferably, a reciprocating rotational motion is employed, combined with a small pressure to advance tissue ablation region 64 through the longitudinal length of the scar tissue to detach the pacemaker lead 66 from the heart wall. The cross-sectional shape of the active electrodes 180a, 180b may be round wires as shown in FIG. 16B, or they may have shaped surfaces to enhance the electric field intensity at the distal surfaces of the active electrodes, as discussed above.

FIGS. 17–21 illustrate other embodiments of tissue ablation region 64 of catheter 60 according to the present invention. In FIGS. 17A and 17B, for example, four active electrodes 190 are secured within an inorganic electrically insulating support member 182. The cross-sectional shape of the active electrodes 190 may be round wires as shown in FIG. 17B, or they may have shaped surfaces to enhance the electric field intensity at the distal surfaces of the active electrodes as described. Another embodiment of tissue ablation region 64, illustrated in FIGS. 18A and 18B, includes a single active electrode 192 secured within support member 182. As before, electrode 192 is preferably rotated as the region 64 is advanced through the scar tissue.

Figure 19A:
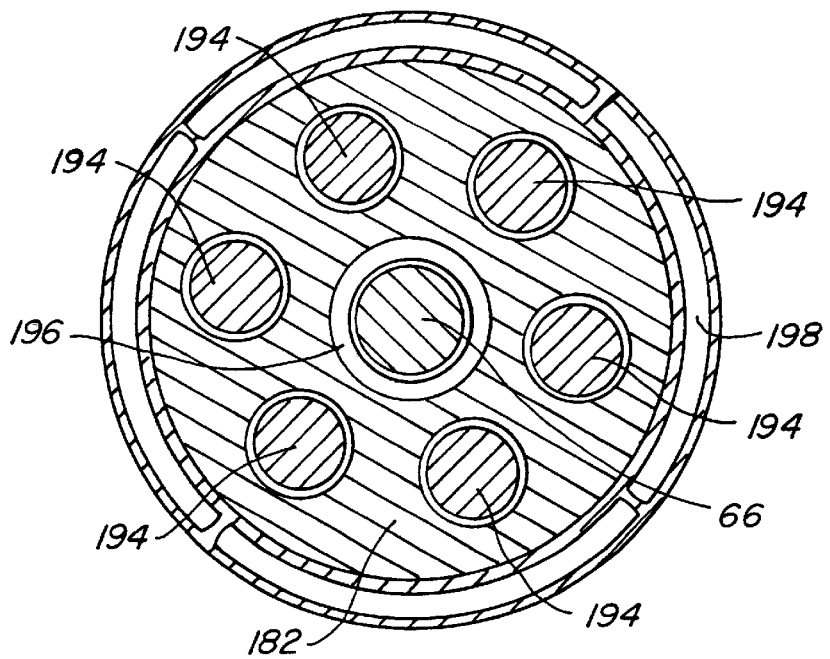
FIGS. 19A and 19B are transverse and longitudinal cross-sectional views, respectively, of a ninth embodiment of the distal ablation region of the catheter.
Figure 19B:
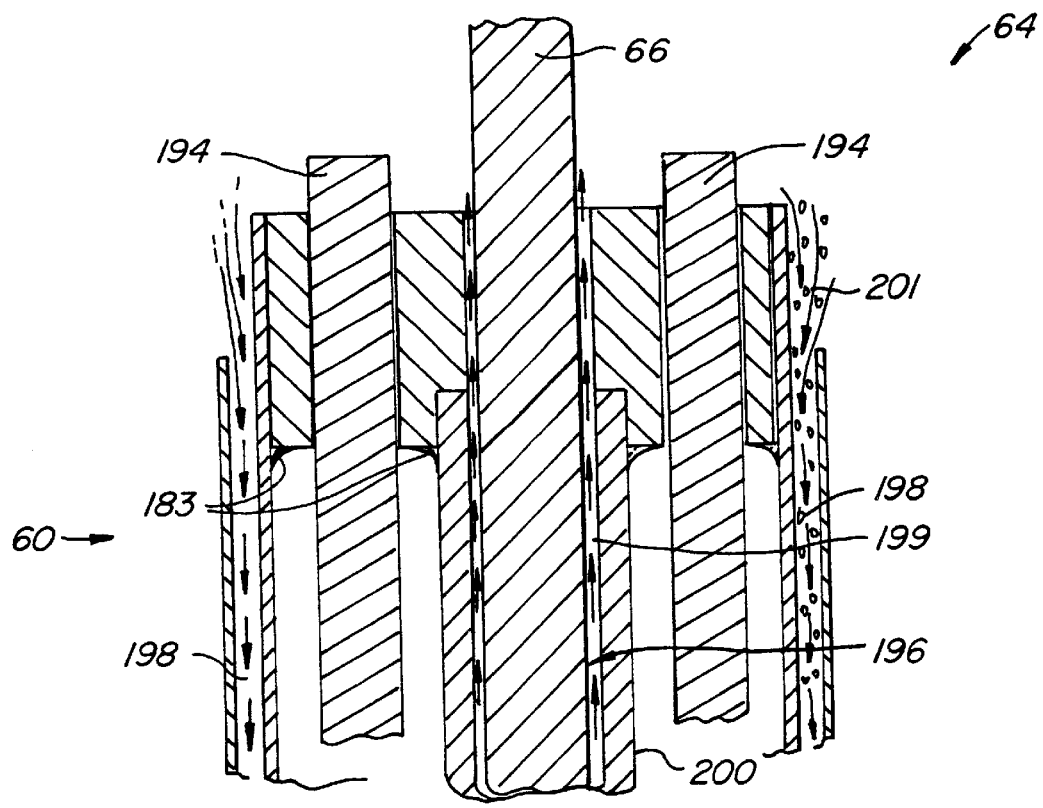

FIGS. 19A and 19B illustrate an embodiment with six active electrodes 194 secured within inorganic support member 182. An annular irrigation lumen 196 and an aspiration lumen 198 are provided to inject electrically conducting fluid 199 and remove gaseous products of ablation 201 from the target site. The return electrode 200 (FIG. 19B) in this embodiment is positioned within the catheter 60 around irrigation lumen 196. As shown, return electrode 200 is an annular electrode that may extend over a portion, or the entire length, of irrigation lumen 196. In this embodiment, it may not be necessary or desirable to rotate the catheter 60 relative to the pacemaker lead 66.

Figure 20A:
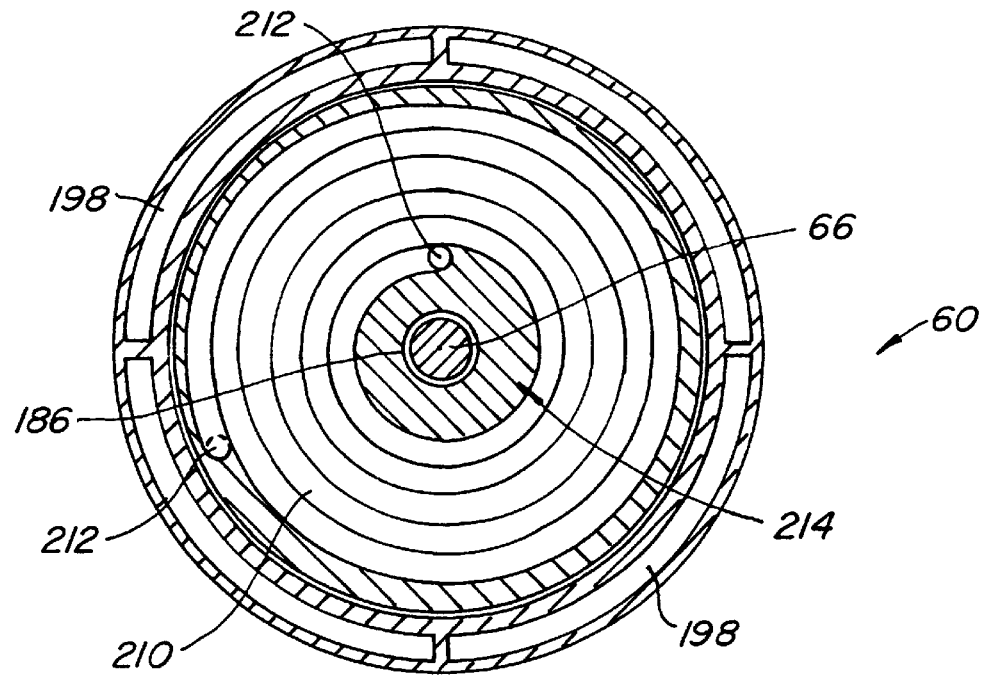
FIGS. 20A and 20B are transverse and longitudinal cross-sectional views, respectively, of a tenth embodiment of the distal ablation region of the catheter.
Figure 20B:
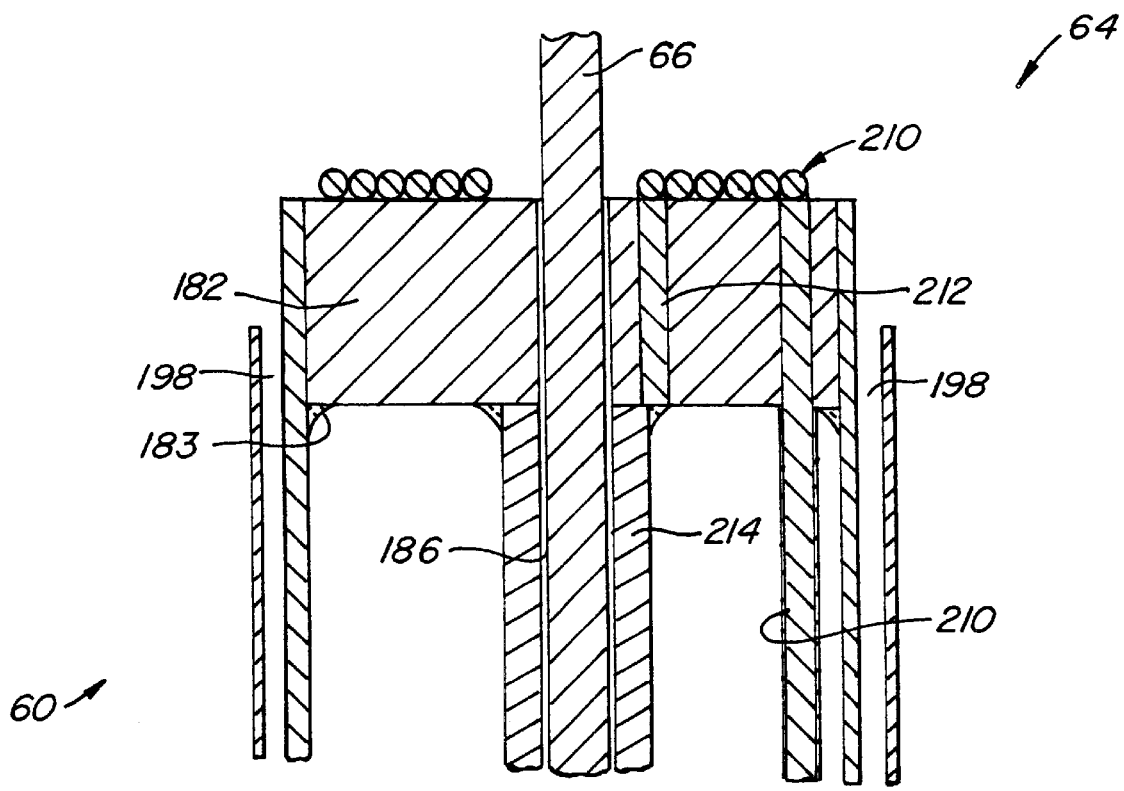
Figure 21A:
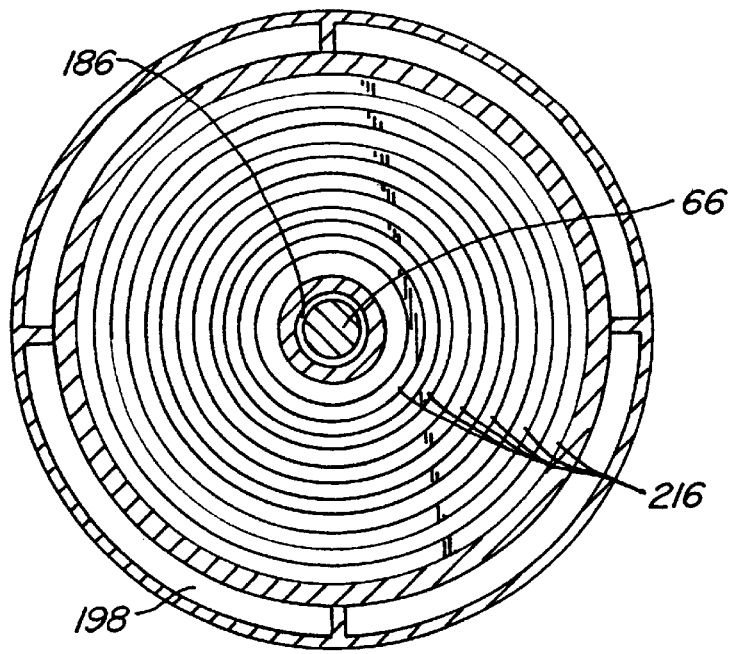
FIGS. 21A and 21B are transverse and longitudinal cross-sectional views, respectively, of an eleventh embodiment of the distal ablation region of the catheter.
Figure 21B:
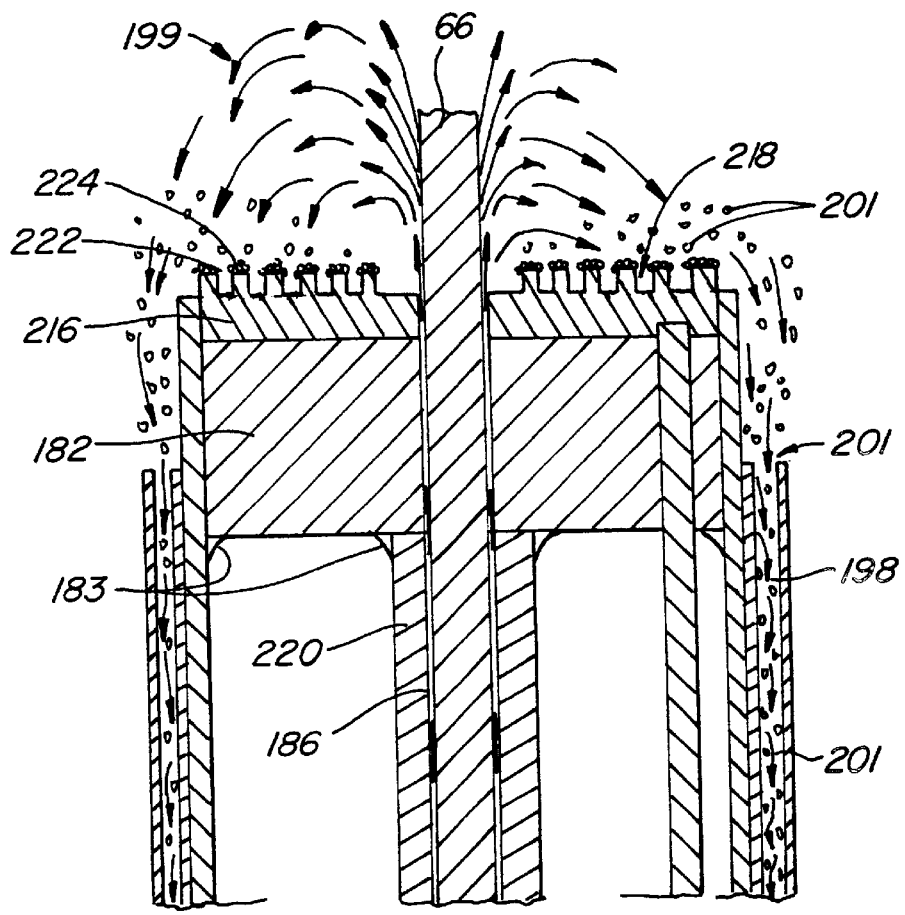

Referring to FIGS. 20A and 20B, yet another embodiment of the invention includes a single active electrode 210 comprising a coiled wire having a plurality of concentric coils 212 tightly and helically wrapped and secured on support member 182 (FIG. 20B). Preferably, the helical coil extends around a return electrode 214 in. concentric configuration, as shown in FIG. 20A. Another embodiment of the invention is shown in FIGS. 21A and 21B. This embodiment is similar to the above embodiment except that the single active electrode 216 defines a series of concentric machined grooves 218 to form concentric circular electrodes 222 surrounding a return electrode 220. The distal edges of electrodes generate regions of high electric field intensities when high frequency voltage is applied between return electrode 220 and concentric active electrodes 222. A vapor layer 224 forms at and around active electrodes 222 with concomitant volumetric removal (ablation) of the scar tissue or occlusive media. The embodiments of FIGS. 20 and 21 are usually advanced through the fibrous scar tissue or occlusive media without rotation.

Figure 22:
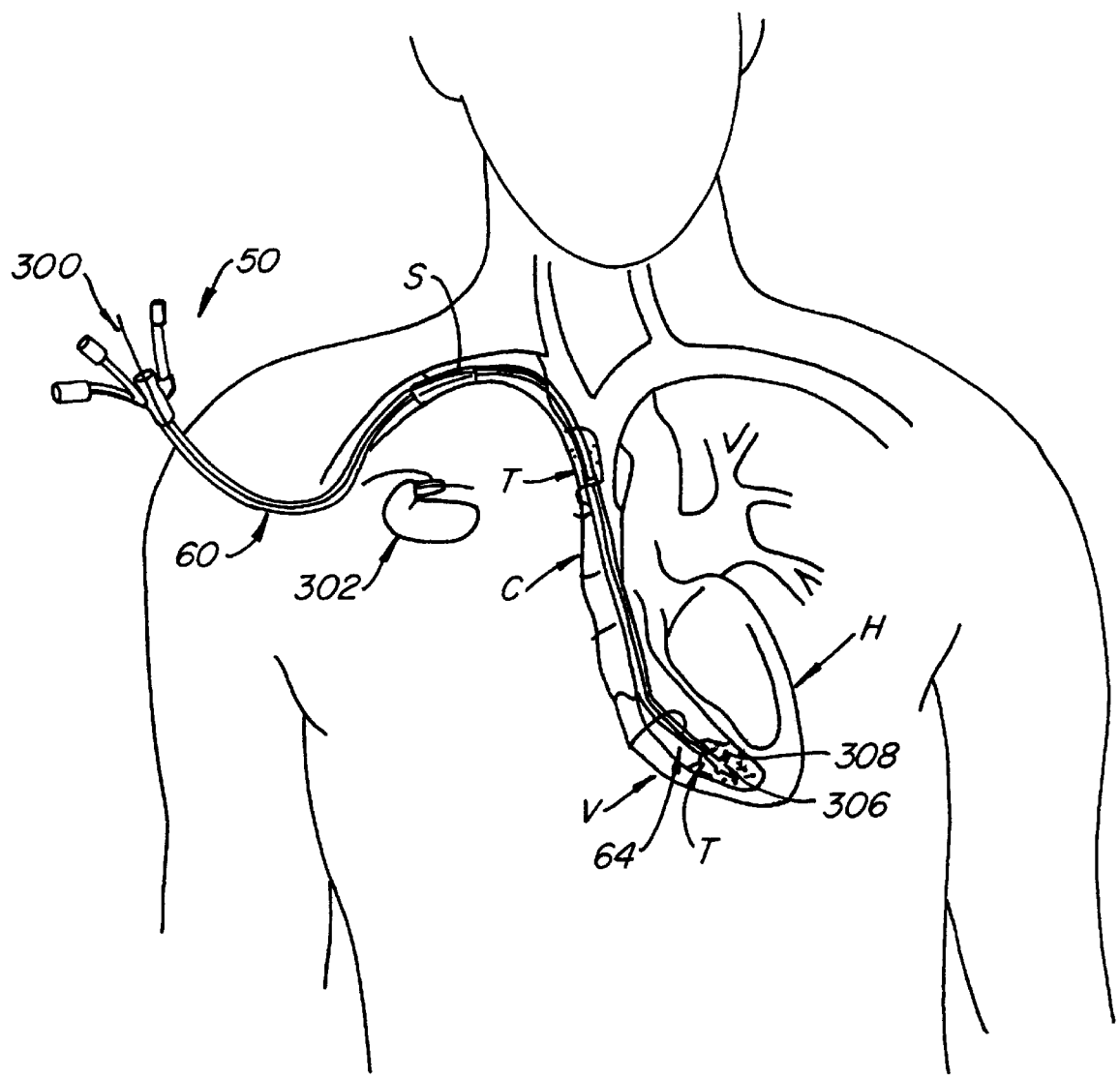
FIG. 22 is a schematic view of the patient's heart and a portion of the cardiovascular system, illustrating a method of removing a pacemaker lead by translating an electrosurgical catheter over the lead.

Referring now to FIGS. 22–25, methods for removing implanted pacemaker leads from a patient's venous system and heart will now be described. As shown in FIG. 22, a typical transvenous endocardial lead 300 connects a pacemaker 302 to the heart H through the right subclavian vein S, and superior vena cava C and down into the heart H. Transvenous endocardial lead 300 is shown specifically in the right ventricle V, although leads to the right atrium A are often used as well. The distal end of lead 300 includes an electrode 306 for electrically stimulating the heart and a plurality of tines 308 to provide fixation of lead 300 within heart H. As discussed above, during chronic implantation, the lead 300 becomes affixed along its side surfaces to inner surfaces of the venous system and at its distal end to heart H through the formation of fibrous scar tissue T.

Figure 24:
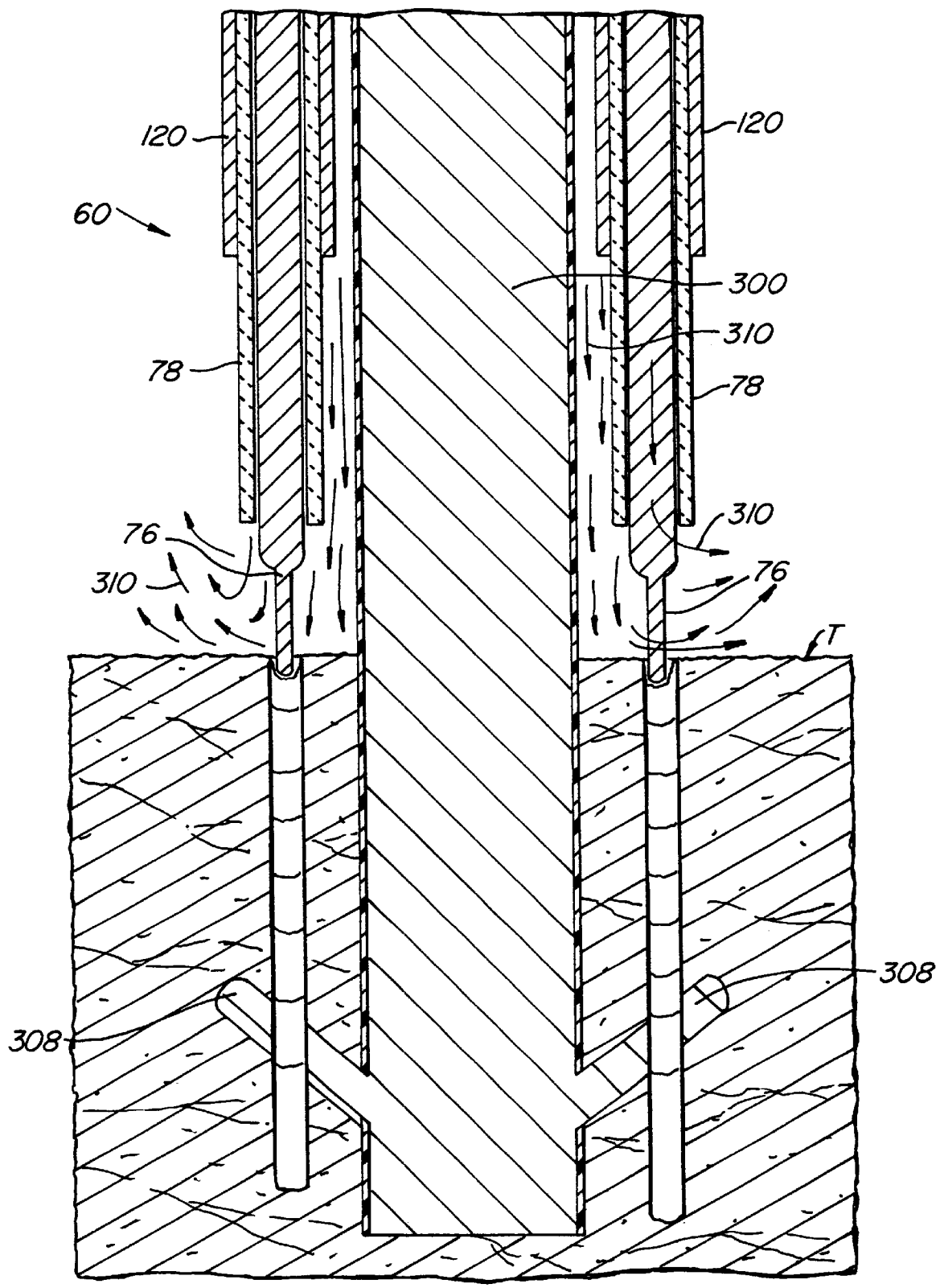
FIG. 24 is an exploded view of the distal portion of an electrosurgical catheter, illustrating a method of removing tissue surrounding the tip of a pacemaker lead.

In use, the proximal end of lead 300 is uncovered surgically and introduced into the central guide lumen 68 of catheter 60 (see FIG. 8). Once catheter 60 is positioned so lead 300 extends into guide lumen 68, the catheter 60 is advanced until distal end 64 of catheter 60 is proximate the fibrous scar tissue T. FIG. 24 illustrates an embodiment in which the lead 300 extends through the entire length of catheter 60. However, it should be clearly understood that the catheter 60 may incorporate a side port near its distal end as described above to allow for a more rapid exchange of the catheter over the pacemaker lead 66. Once the surgeon has reached the point of blockage, electrically conductive fluid is delivered through fluid lumens 126, 128 to the tissue (see FIG. 8A). The rate of fluid flow is controlled with valve 17 (FIG. 1) such that the zone between the tissue and electrode terminals 76 is constantly immersed in the fluid. The power supply 80 is then turned on and adjusted such that a high frequency voltage difference is applied between electrode terminals 76 and return electrode 120. The electrically conductive fluid provides the conduction path (see current flux lines) between electrode terminals 76 and the return electrode 120.

Figure 23:
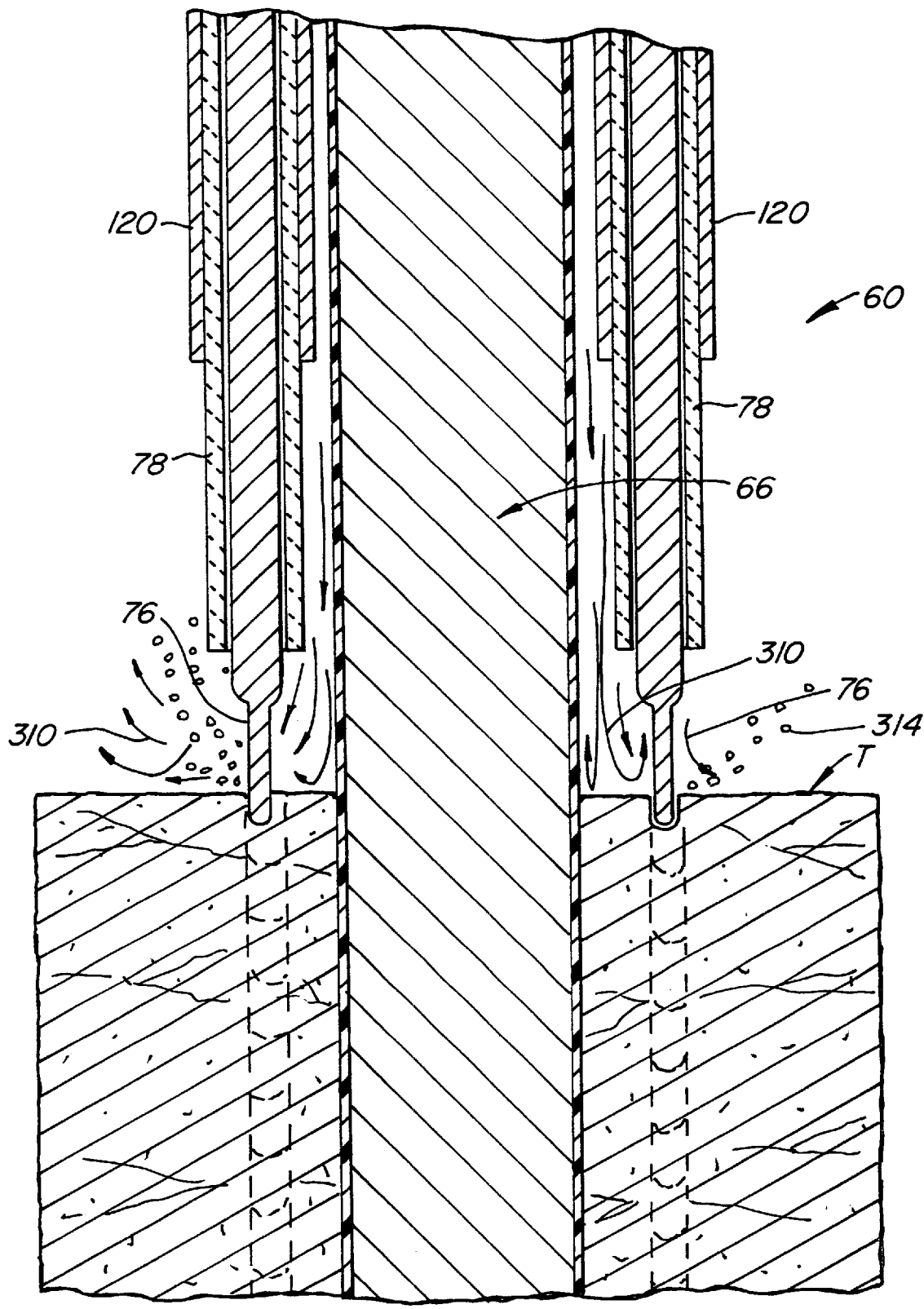
FIG. 23 is an exploded view of the distal portion of an electrosurgical catheter, illustrating a method of removing tissue surrounding the pacemaker lead to separate the lead from the heart.

FIG. 23 illustrates the removal of scar tissue T around the lead 66 in more detail As shown, the high frequency voltage is sufficient to convert the electrically conductive fluid 310 between the target tissue T and electrode terminal(s) 76 into an ionized vapor layer or plasma (not shown). As a result of the applied voltage difference between electrode terminal(s) 76 and the target tissue T (i.e., the voltage gradient across the plasma layer), charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases 314, such as oxygen, nitrogen, carbon dioxide, hydrogen and methane. The short range of the accelerated charged particles within the tissue confines the molecular dissociation process to the surface layer to minimize damage and necrosis to the surrounding tissue.

During the process, the gases 314 may be aspirated through suction lumens is 130, 132 to a vacuum source. In addition, excess electrically conductive fluid, other fluids (e.g., blood), or non-ablated tissue fragments may be aspirated from the target site to facilitate the surgeon's view and to prevent these tissue fragments or the excess fluid from flowing into the patient's heart or vasculature. During ablation of the tissue, the residual heat generated by the current flux lines (typically less than 150° C.), will usually be sufficient to coagulate any severed blood vessels at the site. If not, the surgeon may switch the power supply 80 into the coagulation mode by lowering the voltage to a level below the threshold for fluid vaporization, as discussed above. This simultaneous hemostasis results in less bleeding and facilitates the surgeon's ability to perform the procedure.

As the scar tissue is ablated, the catheter 60 is rotated relative to the lead 66 such that an annular channel of tissue is ablated. The catheter 60 is then advanced through the scar tissue as it ablates this tissue until the lead is released. Catheter 60 is repositioned until once again the distal end is proximate fibrous scar tissue. Application of high frequency electrical energy to electrode terminals is repeated along the entire length of lead 66 until lead is not longer affixed by fibrous scar tissue along its side surface. The voltage will typically be applied continuously during the ablation of a section of tissue. However, the heartbeat may be monitored and the voltage applied in pulses that are suitably timed with the contractions (systole) of the heart.

Once the side surface of lead 66 is released from the fibrous scar tissue T, only fibrous scar tissue proximate distal end of lead 66 at distal face of electrode retains the lead, as shown in FIG. 25. At this point, the electrode terminals 76 may be used to ablate through tines 308, particularly if tines 308 are constructed from common lead materials, such as silicone or polyurethane. Alternatively, electrode assemblies may be deflected radially outward so that the electrode terminals 76 cut or ablate around the tines 308 of the lead tip 306. In other embodiments, the lead 300 may be severed proximal to the tip 306, and the tip 306 left within the heart tissue. In yet other embodiments, traction may be applied to either the proximal end of lead, or to point proximal the tip, such as through a snagging stylet as disclosed in U.S. Pat. Nos. 5,207,683, 5,013,310, and 4,988,347, to withdraw lead from fibrous scar tissue T. Use may also be made of a sheath, as described in U.S. Pat. No. 5,011,482 to Goode et al., to overlay the lead during traction and apply counter traction at a site near the electrode to confine the traction force to an area within the sheath.

The principles of the present invention are also applicable to any body lumen which becomes partially or totally occluded. For example, the present invention is useful in a lumen containing a lumenal prosthesis, such as a stent, stent-graft or graft, which may be metallic, non-metallic or a non-metallic coated metallic structure. A particular advantage of the present invention is the confinement of current flow paths (not shown) between the return electrode (hollow guide wire in the present example) and one or more active electrodes to the vicinity of tissue ablating region of the catheter. This confinement of current flow paths minimizes the undesired flow of current through portions or all of the stent, which may otherwise induce non-specific tissue injury beyond the site of recanization of the occluded lumen. A more complete description of methods and apparatus for ablating occlusive media within body lumens can be found in commonly assigned, co-pending U.S. application Ser. No. 08/874,173 entitled "SYSTEMS AND METHODS FOR ELECTROSURGICAL RESTENOSIS OF BODY LUMENS", filed Jun. 13, 1997, the complete disclosure of which is incorporated herein by reference for all purposes.

What is claimed is:

1. A method for removing a pacemaker lead attached to heart tissue within a patient's body comprising:

positioning an electrode terminal adjacent a portion of the pacemaker lead attached to the heart tissue, the electrode terminal being located at a distal portion of a catheter body; and applying a sufficient high frequency electrical voltage between the electrode terminal and a return electrode to volumetrically remove a portion of the heart tissue attached to the pacemaker lead and further advancing the distal portion of the catheter body along the pacemaker lead to detach said portion of the pacemaker lead from the heart tissue.

2. The method of claim 1 further comprising advancing the distal portion of the catheter body over the pacemaker lead to position the electrode terminal in close proximity with the tissue attached to the lead.

3. The method of claim 1 further comprising removing the pacemaker lead from the patient's body.

4. The method of claim 1 wherein the return electrode is proximal to the electrode terminal such that the electrical current flows from the electrode terminal in a proximal direction to the return electrode away from the tissue.

5. The method of claim 1 wherein the high frequency voltage is applied in the presence of electrically conductive fluid, the method further comprising generating a current flow path through the electrically conductive fluid between the return electrode and the electrode terminal through the electrically conductive fluid.

6. The method of claim 5 wherein the high frequency voltage is sufficient to vaporize the fluid in a thin layer between at least a portion of the electrode terminal and the heart tissue.

7. The method of claim 6 further comprising accelerating charged particles from the vaporized fluid to the heart tissue to cause dissociation of the molecular bonds within the heart tissue.

8. The method of claim 1 further comprising rotating at least the distal portion of the catheter body during the applying step.

9. The method of claim 1 wherein the applying step is carried out by applying high frequency voltage to an electrode array of electrically isolated electrode terminals and the return electrode in the presence of an electrically conductive fluid such that an electrical current flows from each of the electrode terminals, through the electrically conductive fluid, and to the return electrode.

10. The method of claim 9 further comprising independently controlling current flow from at least two of the electrode terminals based on impedance between each of the electrode terminals and the return electrode.

11. The method of claim 1 further comprising aspirating a region around the electrode terminal.

12. The method of claim 1 further comprising directing an electrically conductive fluid through a fluid lumen in the catheter body past the return electrode to the electrode terminal to generate a current flow path between the electrode terminal and the return electrode.

13. The method of claim 1 wherein the pacemaker lead includes a distal tip embedded within heart tissue, the method further comprising removing the distal tip of the pacemaker lead from the heart tissue by applying sufficient high frequency voltage to the electrode terminal to remove at least a portion of the tissue surrounding the tip.

14. The method of claim 13 further comprising deflecting the electrode terminal radially outward to accommodate an enlarged distal tip of the pacemaker lead.

15. The method of claim 13 wherein the distal tip of the pacemaker lead includes one or more tines extending radially outward from the lead, the method further comprising severing the tines.

16. The method of claim 1 wherein the catheter body has an inner lumen sized to accommodate the pacemaker lead, the method further comprising advancing the catheter body over the length of the pacemaker lead to position the electrode terminal adjacent the heart tissue attached to the lead.

17. The method of claim 1 wherein the catheter body includes a distal portion having an inner lumen, a distal hole and an opening in the catheter body proximal to the distal hole, the method further comprising advancing the distal portion of the catheter body over the length of the pacemaker lead such that the lead extends through the distal hole, the inner lumen and the proximal opening.

* * * * *